(12) United States Patent
Zhang et al.

(10) Patent No.: US 10,017,442 B2
(45) Date of Patent: Jul. 10, 2018

(54) METHOD OF USING DIHYDRO-RESVERATROL OR ITS STILBENOID DERIVATIVES AND/OR CHEMICAL VARIANTS IN TREATMENT OF TUMOROUS PATHOLOGIES

(71) Applicant: Hong Kong Baptist University, Hong Kong (HK)

(72) Inventors: Hongjie Zhang, Hong Kong (HK); Siu Wai Tsang, Hong Kong (HK)

(73) Assignee: Hong Kong Baptist University, Hong Kong (HK)

( * ) Notice: Subject to any disclaimer, the term of this patent is extended or adjusted under 35 U.S.C. 154(b) by 0 days.

(21) Appl. No.: 15/849,650

(22) Filed: Dec. 20, 2017

(65) Prior Publication Data

US 2018/0118647 A1 May 3, 2018

Related U.S. Application Data

(60) Continuation-in-part of application No. 15/633,780, filed on Jun. 27, 2017, now Pat. No. 9,877,931, which is a division of application No. 15/351,636, filed on Nov. 15, 2016, now Pat. No. 9,738,581, which is a continuation-in-part of application No. 14/740,410, filed on Jun. 16, 2015, now Pat. No. 9,526,706.

(51) Int. Cl.

| | |
|---|---|
| *A61K 31/05* | (2006.01) |
| *C07C 43/23* | (2006.01) |
| *A61K 31/085* | (2006.01) |
| *A61K 31/09* | (2006.01) |
| *C07C 39/16* | (2006.01) |
| *C07C 37/00* | (2006.01) |
| *C07C 39/15* | (2006.01) |

(52) U.S. Cl.
CPC .............. *C07C 43/23* (2013.01); *A61K 31/05* (2013.01); *A61K 31/085* (2013.01); *A61K 31/09* (2013.01); *C07C 37/003* (2013.01); *C07C 39/15* (2013.01); *C07C 39/16* (2013.01)

(58) Field of Classification Search
CPC ....... C07C 43/23; C07C 37/003; C07C 39/15; C07C 39/16; A61K 31/05; A61K 31/085; A61K 31/09
USPC ........................................................ 514/721
See application file for complete search history.

(56) References Cited

U.S. PATENT DOCUMENTS 9,738,581 B2 * 8/2017 Zhang .................... C07C 43/23
2017/0290782 A1 * 10/2017 Zhang .................... A61K 31/09

OTHER PUBLICATIONS

Lu et al., Influence of Glucuronidation and Reduction Modifications of Resveratrol on its Biological Activities, ChemBioChem, 2013, 14, 1094-1104 (Year: 2013).*
Anroop B. Nair et al., "A simple practice guide for dose conversion between animals and human", Journal of Basic and Clinical Pharmacy, 2016, 7(2), p. 27-31.

* cited by examiner

*Primary Examiner* — Kristin A Vajda
(74) *Attorney, Agent, or Firm* — Idea Intellectual Limited; Margaret A. Burke; Sam T. Yip

(57) ABSTRACT

The present invention relates to a polyphenol derivative of the stilbenoid family, namely trans-3,5,4'-trihydroxybibenzyl, also known as dihydro-resveratrol, as a remedial agent. In particular, the present invention presents the usage of dihydro-resveratrol or its derivatives/chemical variants in the manufacture of a medicament for the treatment of tumors or cancers. The dihydrostilbenes can be used in the treatment or delay of progression of a cancer in a patient or used in a pharmaceutical formulation for the aforementioned purposes.

12 Claims, 25 Drawing Sheets

Control | Cerulein
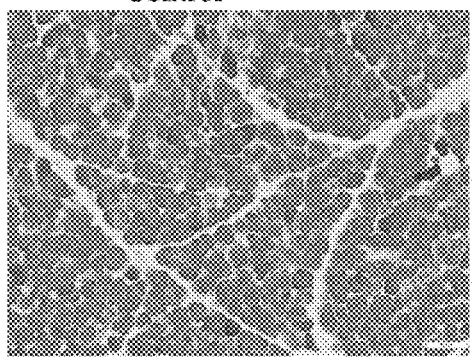 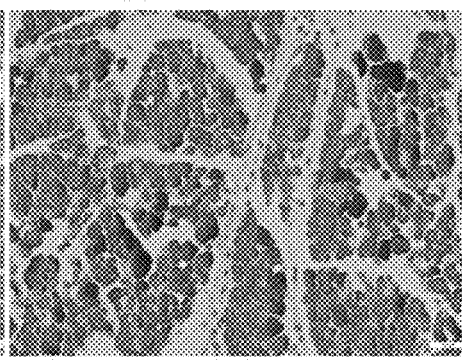
Figure 2A | Figure 2B
Cerulein + D-Res 10mg | Cerulein + D-Res 20mg
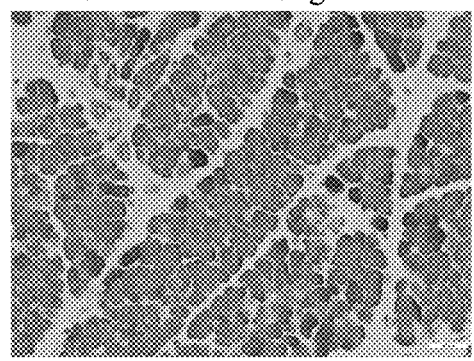 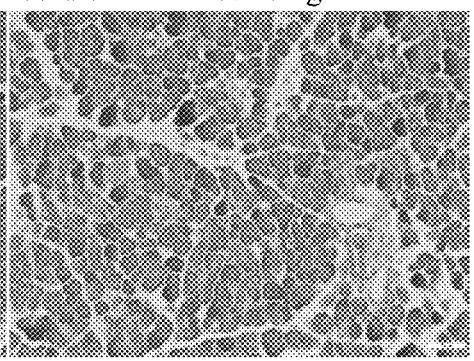
Figure 2C | Figure 2D
Cerulein + D-Res 50mg | D-Res 20mg
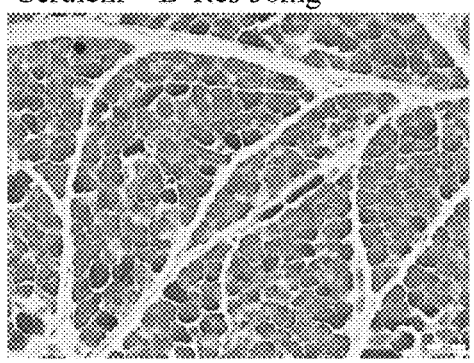 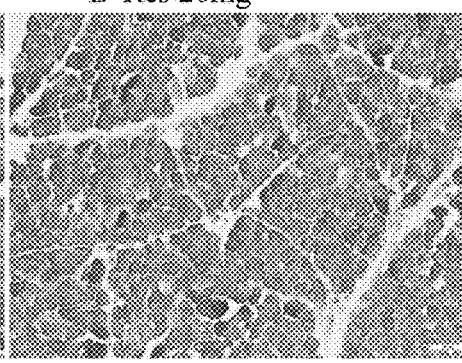
Figure 2E | Figure 2F

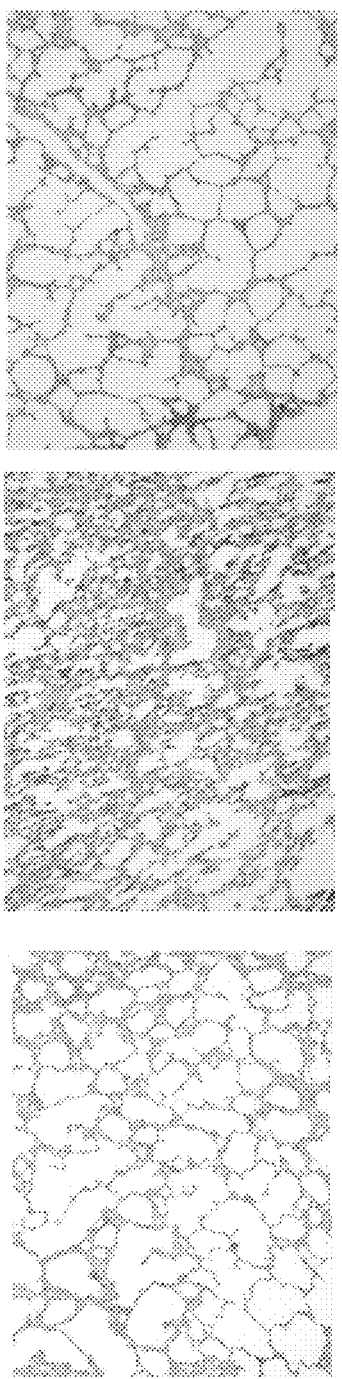
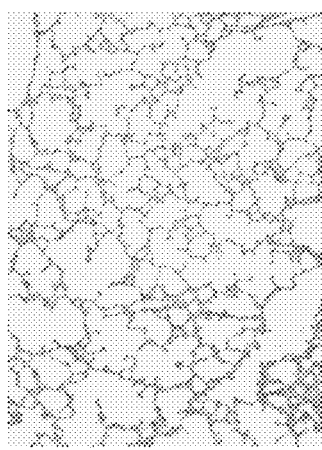
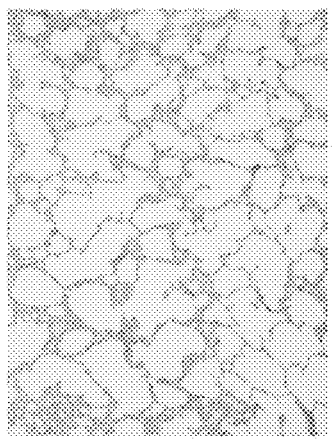
Figure 3A Control
Figure 3B Cerulein
Figure 3C Cerulein + D-Res 10mg
Figure 3D Cerulein + D-Res 20mg
Figure 3E Cerulein + D-Res 50mg

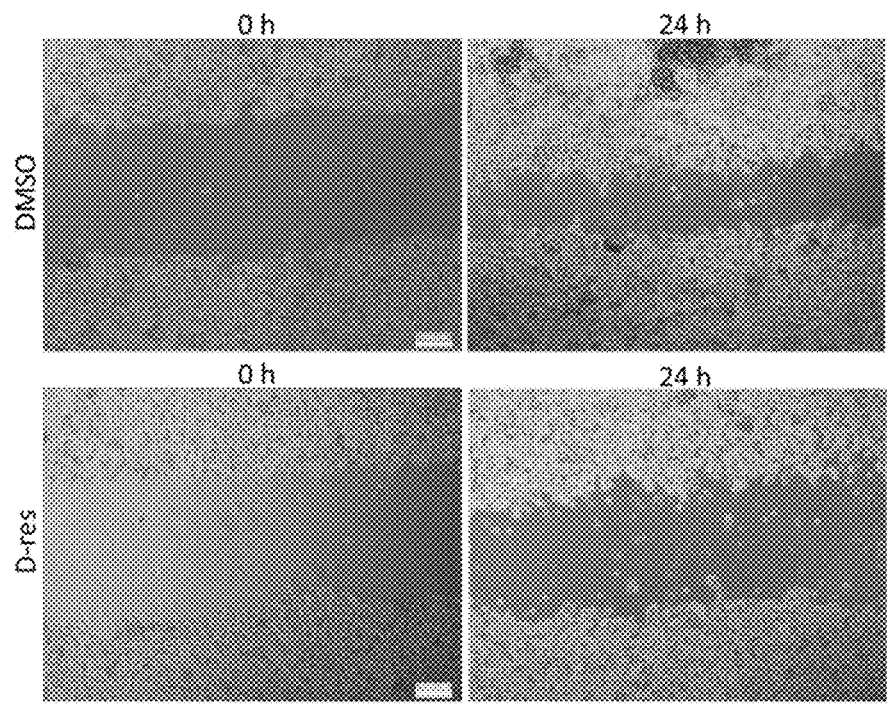
(A)
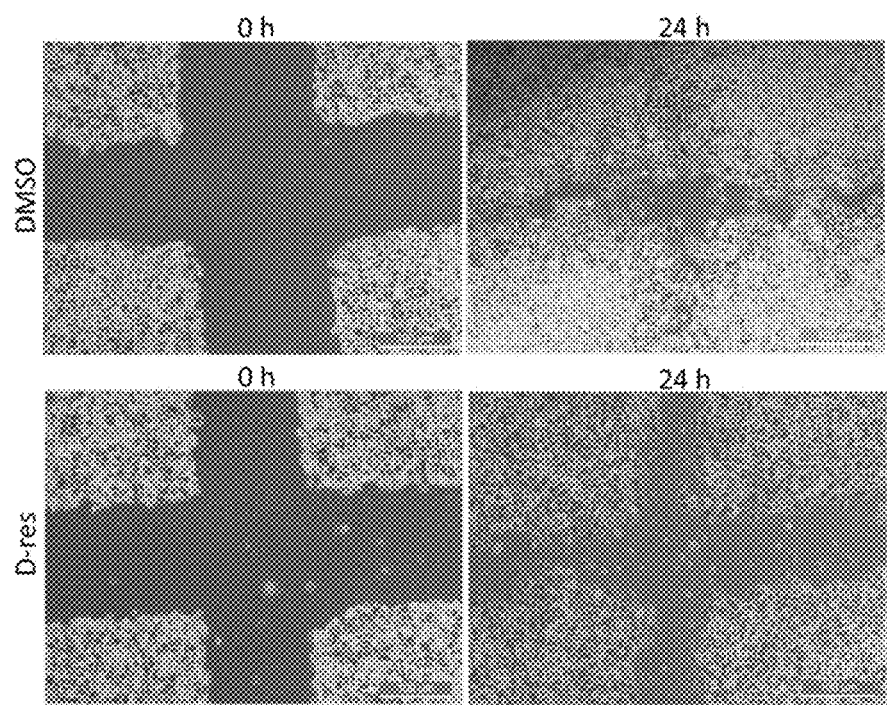
(B)
Figure 19

METHOD OF USING DIHYDRO-RESVERATROL OR ITS STILBENOID DERIVATIVES AND/OR CHEMICAL VARIANTS IN TREATMENT OF TUMOROUS PATHOLOGIES

CROSS-REFERENCE TO RELATED APPLICATIONS

The present application is a continuation-in-part application of U.S. non-provisional application Ser. No. 15/633,780 filed on Jun. 27, 2017 which is a divisional application of the U.S. non-provisional patent application Ser. No. 15/351,636 filed on Nov. 15, 2016 which is a continuation-in-part application of the U.S. non-provisional patent application Ser. No. 14/740,410 filed on Jun. 16, 2015, which the disclosures are hereby incorporated by reference in their entirety.

FIELD OF INVENTION

The present invention relates to a polyphenol derivative of the stilbenoid family, namely trans-3,5,4'-trihydroxybibenzyl, also known as dihydro-resveratrol, as a remedial agent. In particular, the present invention presents the usage of dihydro-resveratrol or its derivatives/chemical variants in the manufacture of a medicament for the treatment of tumors or cancers. The dihydrostilbenes can be used in the treatment or delay of progression of a cancer in a patient or used in a pharmaceutical formulation for the aforementioned purposes.

BACKGROUND OF INVENTION

Tumor, particularly in the malignant form, commonly known as cancer, is one of the leading causes of death and accounts for about 13% of all deaths worldwide. In general, tumor cells are defined as highly proliferative as they continue to divide and grow evading normal inhibitory controls, such as programmed cell death and cell cycle arrest. According to the report of cancer incidence in 2015 by the United States National Cancer Institute, breast, lung, prostate and colorectal carcinomas as well as melanoma are diagnosed with the greatest frequency. As stated in the American Community Survey 2015, lung and colorectal carcinomas led to the highest death rates amongst the common cancers. Most of the current mainstay antitumor agents are used to induce cell death and/or cell cycle arrest in the incipient tumor cells, so that tumor development or progression is expected to be halted. Despite numerous chemotherapeutic agents are available on the market today, many of them either possess narrow therapeutic indices or exert undesirable side-effects. Fluorouracil (5-FU), an antimetabolite, is one of the most commonly used drugs in cancer treatment as it improves the survival of patients with various cancers whereas it imposes the largest impact in colorectal cancer. However, this antimetabolite causes diarrhea, nausea, mouth scores, etc. in patients and thus leads to their loss of body weight and/or poor appetite. On the other hand, malignant tumor cells often develop resistance in response to the use of single cytotoxic agents or a group of similar agents; therefore, the effectiveness and efficacy of many chemotherapeutic treatments become very limited. Till now, chemotherapy resistance is a major concern in the medical management of patients suffered from tumorous pathologies. Taken together, discovery and development of new and potent antitumor remedies are urgently needed.

Over the past decades, a number of pharmacological studies have been focused on the use of drug-like small molecules as chemotherapeutic agents derived from herbal constituents, particularly polyphenolic stilbenoids. In fact, stilbenoids are a category of compounds composed of a general C6-C2-C6 structure, and they are often isolated as monomers and oligomers for their applications as botanical supplements or active constituents in medicinal preparations. As suggested by a growing body of evidence that stilbenoids are potent antioxidants as most of them are produced as phytoalexins against abiotic and biotic stress factors. In addition, some of the stilbenoids have been reported with anti-inflammatory activity and anti-diabetic potential.

It is an objective of the present invention to provide a method of using dihydro-resveratrol as an anti-tumor agent in a subject.

Citation or identification of any reference in this section or any other section of this application shall not be construed as an admission that such reference is available as prior art for the present application.

SUMMARY OF INVENTION

Accordingly, the objective of the present invention relates to a method of using an effective amount of dihydro-resveratrol or its stilbenoid derivatives and/or chemical variants in the manufacture of a medicament for the treatment of tumors or cancers. The dihydrostilbenes can be used in the treatment or delay of progression of a cancer in a patient or used in a pharmaceutical formulation for the aforementioned purposes.

In a first embodiment of a first aspect of the present invention there is provided a method of treating acute inflammatory condition of the pancreas and associated systemic complications by administering to a subject in needs thereof a composition comprising an effective amount of a stilbenoid derivative which comprises a compound of formula (1),

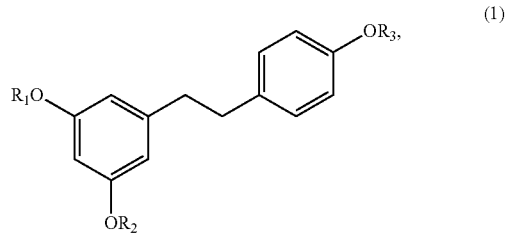

(1)

wherein $R_1$, $R_2$ and $R_3$ are each independently selected from an alkyl group. The term "alkyl", alone or in combination with other groups, includes reference to a straight chain alkyl moiety having 1, 2, 3, 4, 5 or 6 carbon atoms. The term is further exemplified by such groups as methyl, ethyl, propyl (n-propyl or isopropyl), butyl (n-butyl, sec-butyl and tert-butyl), pentyl, hexyl and the like, and the derivatives or chemical variants thereof; or a mixture of said compound, the derivative and/or chemical variants thereof.

In a second embodiment of a first aspect of the present invention there is provided a method of treating acute inflammatory condition of the pancreas and associated systemic complications wherein the stilbenoid derivative is trans-3,5,4'-trihydroxybibenzyl, or dihydro-resveratrol, which is a compound of formula (2):

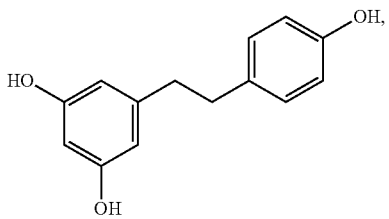

(2)

and the derivatives or chemical variants thereof; or a mixture of said compound, the derivative and/or chemical variants thereof.

In a third embodiment of the first aspect of the present invention there is provided a method of treating acute inflammatory condition of the pancreas and associated systemic complications wherein the subject is a human or an animal.

In a fourth embodiment of the first aspect of the present invention there is provided a method of treating acute inflammatory condition of the pancreas and associated systemic complications wherein the composition is administered orally.

In a fifth embodiment of the first aspect of the present invention there is provided a method of treating acute inflammatory condition of the pancreas and associated systemic complications wherein the acute inflammatory condition of the pancreas comprises all forms of acute pancreatitis and the associated systemic complications comprise pulmonary injury.

In a sixth embodiment of the first aspect of the present invention there is provided a method of treating acute inflammatory condition of the pancreas and associated systemic complications wherein said composition is administered at no less than 20 mg/kg to said subject for no less than 3 times a day.

In a seventh embodiment of the first aspect of the present invention there is provided a method of treating acute inflammatory condition of the pancreas and associated systemic complications wherein said composition is administered at no less than 3.24 mg/kg to said subject for no less than 3 times a day.

In a first embodiment of a second aspect of the present invention there is provided a method for preparing a compound of molecular formula $C_{14}H_{14}O_3$ and of formula (2),

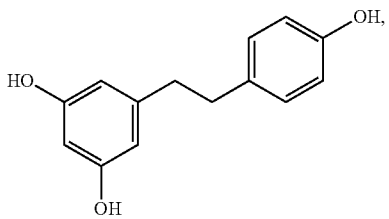

(2)

which is a stilbenoid derivative having a chemical name of trans-3,5,4'-trihydroxybibenzyl by hydrogenating of trans-resveratrol.

In a second embodiment of the second aspect of the present invention there is provided a method of preparing the compound of molecular formula $C_{14}H_{14}O_3$ and of formula (2) wherein the hydrogenating of trans-resveratrol comprises steps of stirring a solution of trans-resveratrol in anhydrous ethanol (EtOH) at room temperature under 5 atm $H_2$ pressure in the presence of 10% Pd/C for 8 hours;
filtering off the catalyst from the stirred solution;
evaporating the filtrate in vacuum to produce a residue;
eluting the residue using silica gel chromatographic separation with petroleum ether and ethyl acetate (1:1) to produce dihydro-resveratrol.

In a first embodiment of the third aspect of the present invention there is provided a compound for suppressing a fibrotic mediator of stellate cells present in an internal organ of a subject in need with a formula of

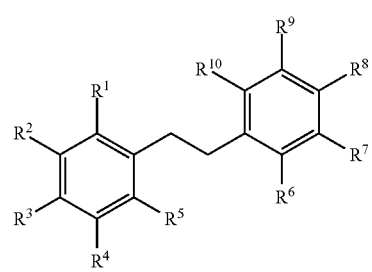

(3)

wherein
$R^2$ and $R^4$ are each independently selected from —$OR^{11}$ and —$OC(O)R^{11}$;
$R^1$, $R^3$, $R^5$, $R^6$, $R^7$, $R^8$, $R^9$ and $R^{10}$ are each independently selected from hydrogen, halogen, trifluoromethyl, —$OR^{11}$ and —$OC(O)R^{11}$; or $R^2$ and $R^3$, or $R^7$ and $R^8$ may be taken together with the carbon atoms to which they are attached to form a cyclic group;
$R^{11}$ is independently hydrogen or selected from hydrocarbyl and heterocyclyl, either of which is optionally substituted with 1, 2, 3, 4 or 5 $R^{12}$;
$R^{12}$ is independently selected from halogen, trifluoromethyl, cyano, nitro, oxo, —$OR^{13}$, —$C(O)R^{14}$, —$C(O)N(R^{13})R^{14}$, —$C(O)OR^{13}$, —$OC(O)R^{14}$, —$S(O)_2R^{13}$, —$S(O)_2N(R^{13})R^{14}$, —$N(R^{13})R^{14}$;
$R^{13}$ and $R^{14}$ are each independently hydrogen or selected from hydrocarbyl and heterocyclyl, either of which is optionally substituted with 1, 2, 3, 4 or 5 substituents independently selected from halogen, cyano, amino, hydroxy, $C_{1-6}$ alkyl and $C_{1-6}$alkoxy;
or an enantiomer thereof;
or a pharmaceutically acceptable salt or prodrug thereof;
or a mixture of said compound, the derivative and/or chemical variants thereof.

In a second embodiment of the third aspect of the present invention there is provided a compound for suppressing a fibrotic mediator of stellate cells present in an internal organ of a subject in need with a formula of

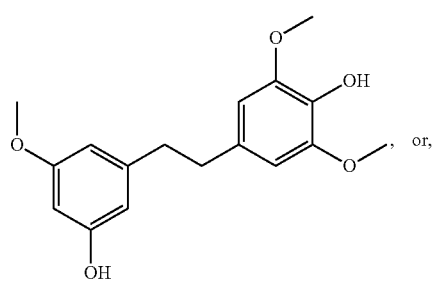

(i)

or,

-continued

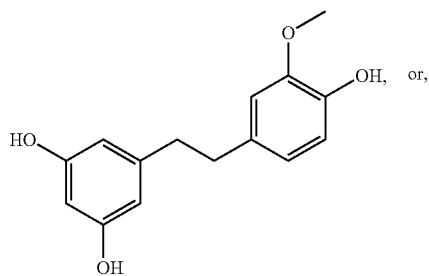
(ii)

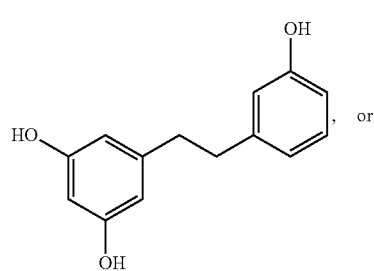
(iii)

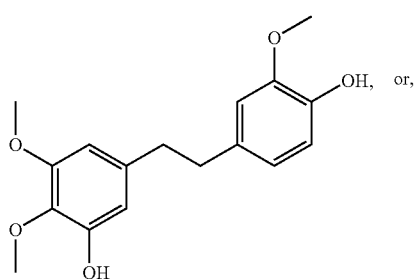
(iv)

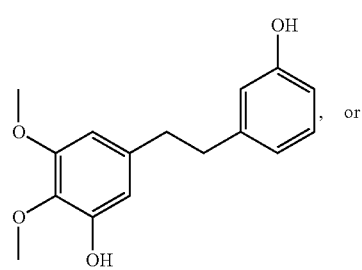
(v)

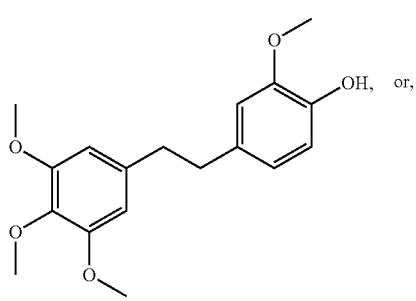
(vi)

-continued

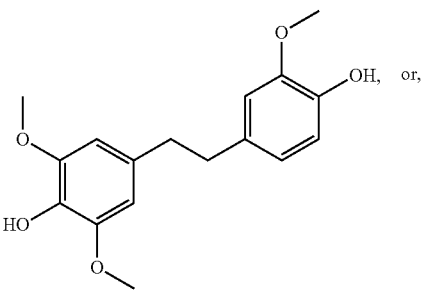
(vii)

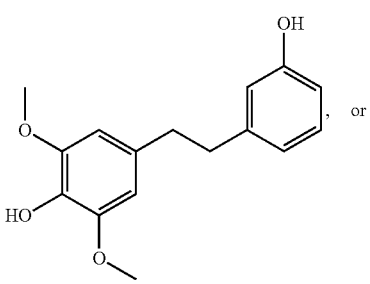
(viii)

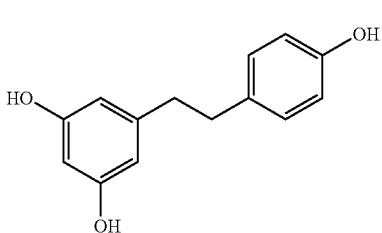
(2)

In a first embodiment of the fourth aspect of the present invention there is provided a method for suppressing fibrotic mediator(s) in stellate cells present in an internal organ of a subject in need by using a composition comprising compounds i to viii or dihydro-resveratrol.

In a second embodiment of the fourth aspect of the present invention there is provided a method for suppressing fibrotic mediator(s) in stellate cells present in an internal organ of a subject in need wherein the composition is administered to a subject in need thereof with a dosage of at least 1.622 mg/kg/day wherein said composition is consisted of a compound with a formula of

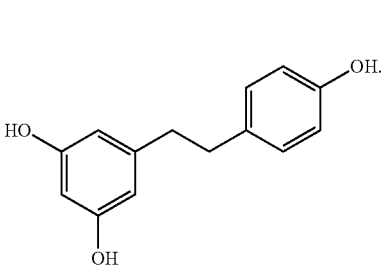
(2)

In a third embodiment of the fourth aspect of the present invention there is provided a method for suppressing fibrotic mediator(s) in stellate cells present in an internal organ of a subject in need wherein the said subject is human.

In a fourth embodiment of the fourth aspect of the present invention there is provided a method for suppressing fibrotic mediator(s) in stellate cells present in an internal organ of a subject in need wherein the composition is administered orally to said subject in need thereof.

In a fifth embodiment of the fourth aspect of the present invention there is provided a method for suppressing fibrotic mediator(s) in stellate cells present in an internal organ of a subject in need wherein the internal organ comprises pancreas, liver, kidney and lung.

In a first embodiment of the fifth aspect of the present invention there is provided a compound for treating pancreatogenic diabetes (or Type 3c diabetes milieus) in a subject in need with a therapeutically effective amount of a formula of

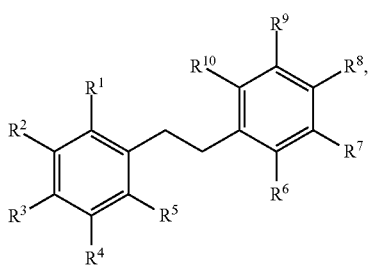

(3)

wherein $R^2$ and $R^4$ are each independently selected from —$OR^{11}$ and —$OC(O)R^{11}$;

$R^1$, $R^3$, $R^5$, $R^6$, $R^7$, $R^8$, $R^9$ and $R^{10}$ are each independently selected from hydrogen, halogen, trifluoromethyl, —$OR^{11}$ and —$OC(O)R^{11}$; or $R^2$ and $R^3$, or $R^7$ and $R^8$ may be taken together with the carbon atoms to which they are attached to form a cyclic group;

$R^{11}$ is independently hydrogen or selected from hydrocarbyl and heterocyclyl, either of which is optionally substituted with 1, 2, 3, 4 or 5 $R^{12}$;

$R^{12}$ is independently selected from halogen, trifluoromethyl, cyano, nitro, oxo, —$OR^{13}$, —$C(O)R^{14}$, —$C(O)N(R^{13})R^{14}$, —$C(O)OR^{13}$, —$OC(O)R^{14}$, —$S(O)_2R^{13}$, —$S(O)_2N(R^{13})R^{14}$, —$N(R^{13})R^{14}$;

$R^{13}$ and $R^{14}$ are each independently hydrogen or selected from hydrocarbyl and heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy;

or an enantiomer thereof;

or a pharmaceutically acceptable salt or prodrug thereof;

or a mixture of said compound, the derivative and/or chemical variants thereof.

In a second embodiment of the fifth aspect of the present invention there is provided a method for treating pancreatogenic diabetes (or Type 3c diabetes milieus) in a subject in need by using a composition comprising compounds of a formula of

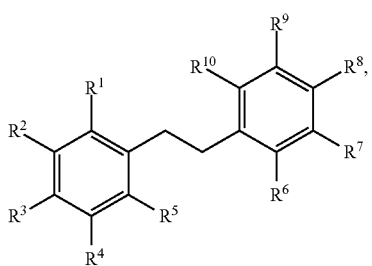

(3)

wherein $R^2$ and $R^4$ are each independently selected from —$OR^{11}$ and —$OC(O)R^{11}$;

$R^1$, $R^3$, $R^5$, $R^6$, $R^7$, $R^8$, $R^9$ and $R^{10}$ are each independently selected from hydrogen, halogen, trifluoromethyl, —$OR^{11}$ and —$OC(O)R^{11}$; or $R^2$ and $R^3$, or $R^7$ and $R^8$ may be taken together with the carbon atoms to which they are attached to form a cyclic group;

$R^{11}$ is independently hydrogen or selected from hydrocarbyl and heterocyclyl, either of which is optionally substituted with 1, 2, 3, 4 or 5 $R^{12}$;

$R^{12}$ is independently selected from halogen, trifluoromethyl, cyano, nitro, oxo, —$OR^{13}$, —$C(O)R^{14}$, —$C(O)N(R^{13})R^{14}$, —$C(O)OR^{13}$, —$OC(O)R^{14}$, —$S(O)_2R^{13}$, —$S(O)_2N(R^{13})R^{14}$, —$N(R^{13})R^{14}$;

$R^{13}$ and $R^{14}$ are each independently hydrogen or selected from hydrocarbyl and heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy;

or an enantiomer thereof;

or a pharmaceutically acceptable salt or prodrug thereof;

or a mixture of said compound, the derivative and/or chemical variants thereof.

In a third embodiment of the fifth aspect of the present invention there is provided a method for treating pancreatogenic diabetes (or Type 3c diabetes milieus) in a subject in need wherein the composition is administered to a subject in need thereof with a dosage of at least 1.622 mg/kg/day wherein said composition is consist of a compound with a formula of

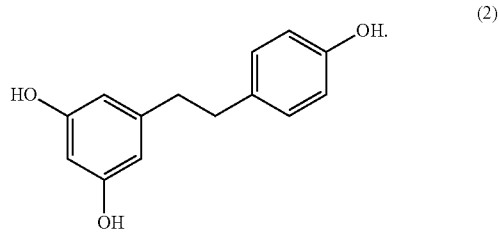 [SMILES: Oc1ccc(CCc2cc(O)cc(O)c2)cc1]

(2)

In a fourth embodiment of the fifth aspect of the present invention there is provided a method for treating pancreatogenic diabetes (or Type 3c diabetes milieus) in a subject in need wherein the said subject is human.

In a fifth embodiment of the fifth aspect of the present invention there is provided a method for treating pancreatogenic diabetes (or Type 3c diabetes milieus) in a subject in need wherein the composition is administered orally to said subject in need thereof.

In a first embodiment of the sixth aspect of the present invention there is provided a compound for treating pancreatogenic diabetes (or Type 3c diabetes milieus) in a subject in need with a therapeutically effective amount of a formula of (i)
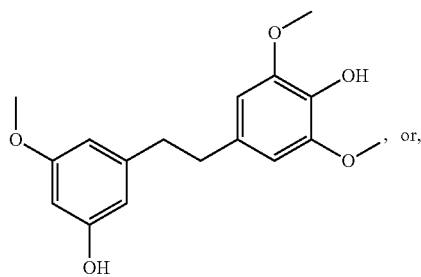
, or, (ii)
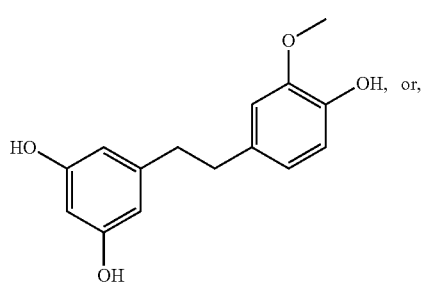
, or, (iii)
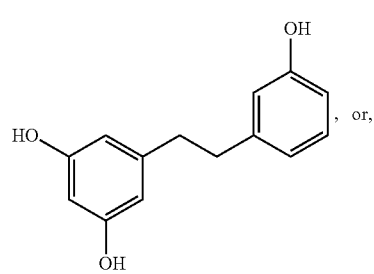
, or, (iv)
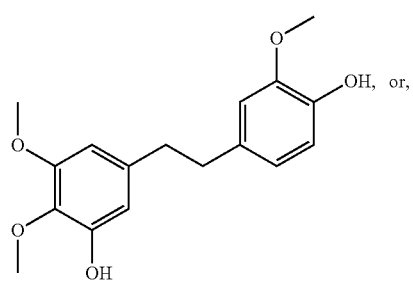
, or, (v)
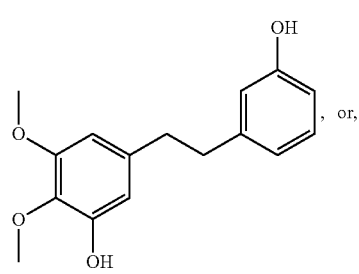
, or, (vi)
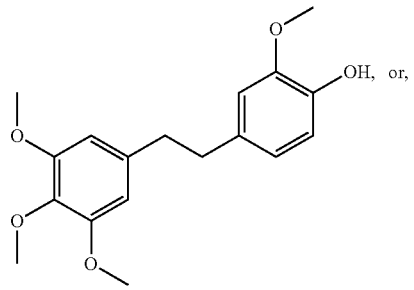
, or, (vii)
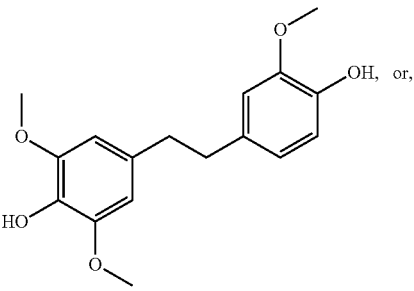
, or, (viii)
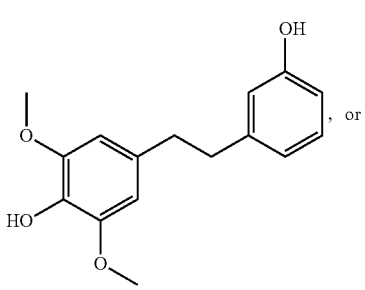
, or (2)
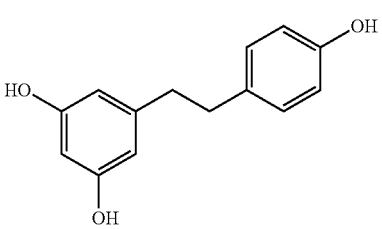

In a second embodiment of the sixth aspect of the present invention there is provided a method for treating pancreatogenic diabetes (or Type3c diabetes milieus) in a subject wherein the composition is administered to a subject in need thereof with a dosage of at least 1.622 mg/kg/day wherein said composition is consist of a compound with a formula of (2)
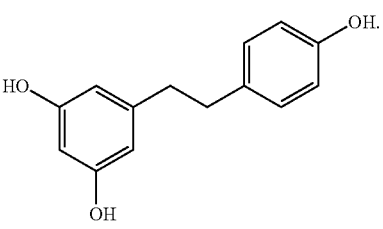

In a third embodiment of the sixth aspect of the present invention there is provided a method for treating pancreatogenic diabetes (or Type3c diabetes milieus) in a subject wherein the said subject is human.

In a first embodiment of the seventh aspect of the present invention, there is provided a method of treating colorectal melanoma and pancreatic carcinoma by administering to a subject in need thereof an effective dosage of a compound comprising a formula (2)

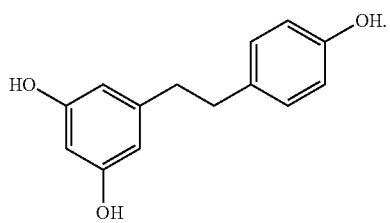

(2)

In a second embodiment of the seventh aspect of the present invention, said compound is dihydro-resveratrol.

In a third embodiment of the seventh aspect of the present invention, said compound is trans-3,5,4'-trihydroxybibenzyl.

In a forth embodiment of the seventh aspect of the present invention, said effective dosage ranges from 1.62 mg/kg to 8.13 mg/kg in body weight per day. Said effective dosage is 8.13 mg/kg in body weight per day.

In a fifth embodiment of the seventh aspect of the present invention, said subject is human.

In a sixth embodiment of the seventh aspect of the present invention, said compound is administered in situ to site of the colorectal melanoma and pancreatic carcinoma or intraperitoneally to said subject in need thereof.

In a seventh embodiment of the seventh aspect of the present invention, said compound is administered every other day for an effective period of time. The effective period of time is no less than 21 days.

Those skilled in the art will appreciate that the invention described herein is susceptible to variations and modifications other than those specifically described.

The invention includes all such variation and modifications. The invention also includes all of the steps and features referred to or indicated in the specification, individually or collectively and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the invention and apply throughout. Unless otherwise defined, all other technical terms used herein have the same meaning as commonly understood to one of ordinary skill in the art to which the invention belongs.

Other aspects and advantages of the invention will be apparent to those skilled in the art from a review of the ensuing description.

BRIEF DESCRIPTION OF DRAWINGS

The above and other objects and features of the present invention will become apparent from the following description of the present invention, when taken in conjunction with the accompanying drawings, in which:

FIGS. 2A to 2F show the architecture and morphological alteration in pancreatic tissues of control group (FIG. 2A), cerulein group (FIG. 2B) and dihydro-resveratrol treatment groups (D-Res) (FIGS. 2C to 2F) by means of hematoxylin and eosin (H&E) staining. Images are shown with a scale bar of 50 μm.

FIGS. 3A to 3E show the architecture and morphological alteration in pulmonary tissues of control group (FIG. 3A), cerulein group (FIG. 3B) and dihydro-resveratrol treatment groups (D-Res) (FIGS. 3C to 3E) by means of H&E staining. Images are shown with a magnification of 200×.

Figure 6A:
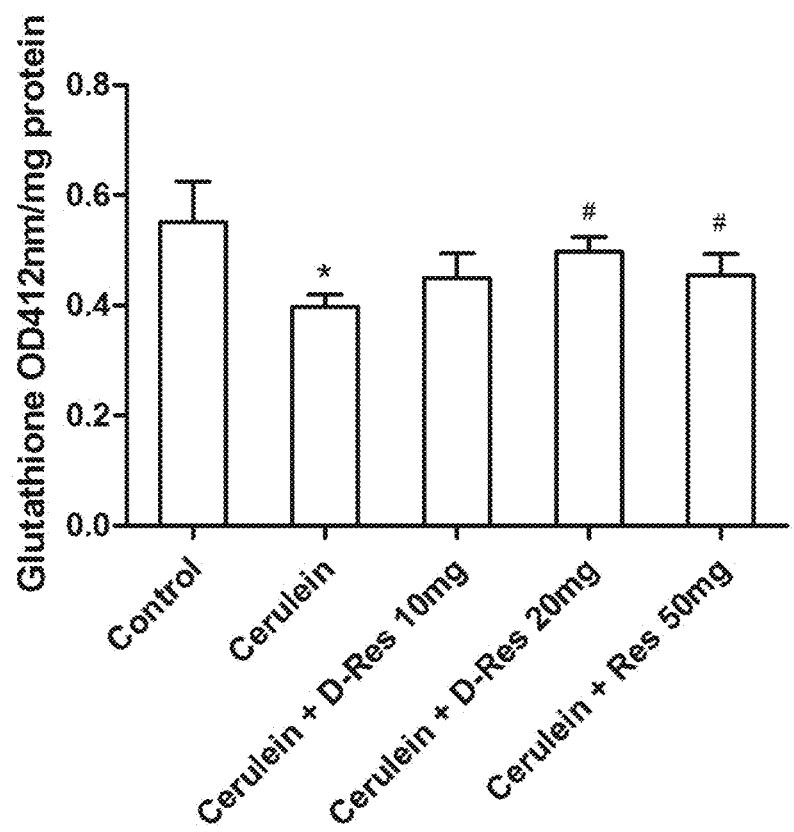
FIG. 6A shows the measurement of glutathione levels in pancreatic tissues of control group, cerulein group and dihydro-resveratrol treatment groups (D-Res) by means of colorimetric spectrophotometry. A p-value of less than 0.05 is considered as statistically significant. *p<0.05 when comparing with control group whereas #p<0.05 comparing with cerulein group.
Figure 6B:
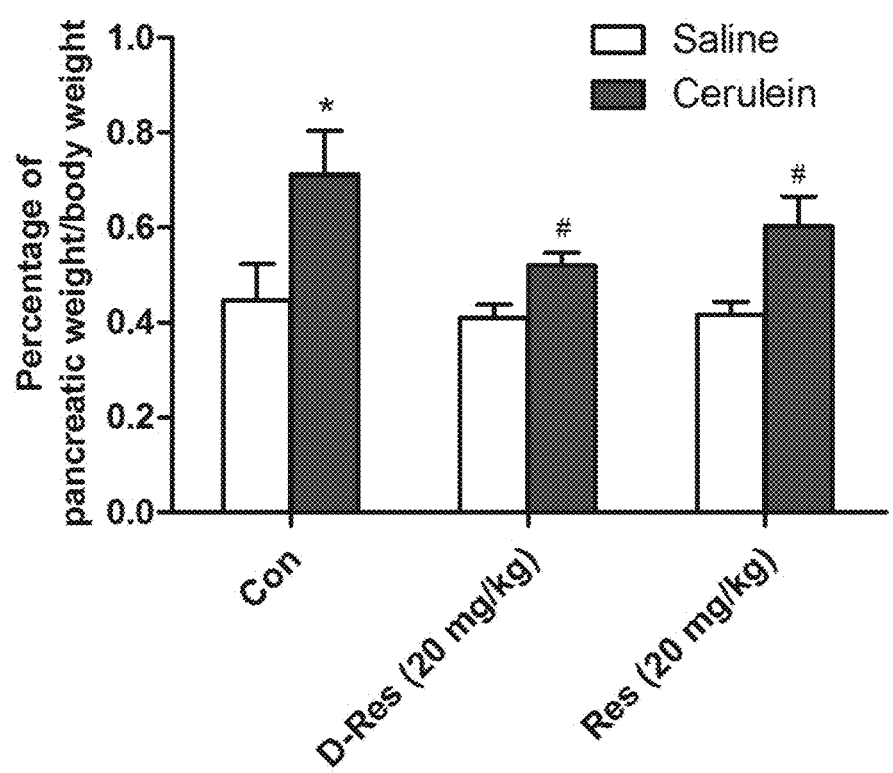

FIG. 6B shows the ameliorative effect of dihydro-resveratrol (D-res) and trans-resveratrol (Res) on reducing water content as a result of pancreatic edema in rats with cerulein-induced acute pancreatitis. The obtained weights are expressed as a ratio percentage of pancreatic weight to body mass. A p-value of less than 0.05 is considered as statistically significant. *p<0.05 when comparing with saline-treated control group (Con) whereas #p<0.05 comparing with cerulein-treated control group.

Figure 7:
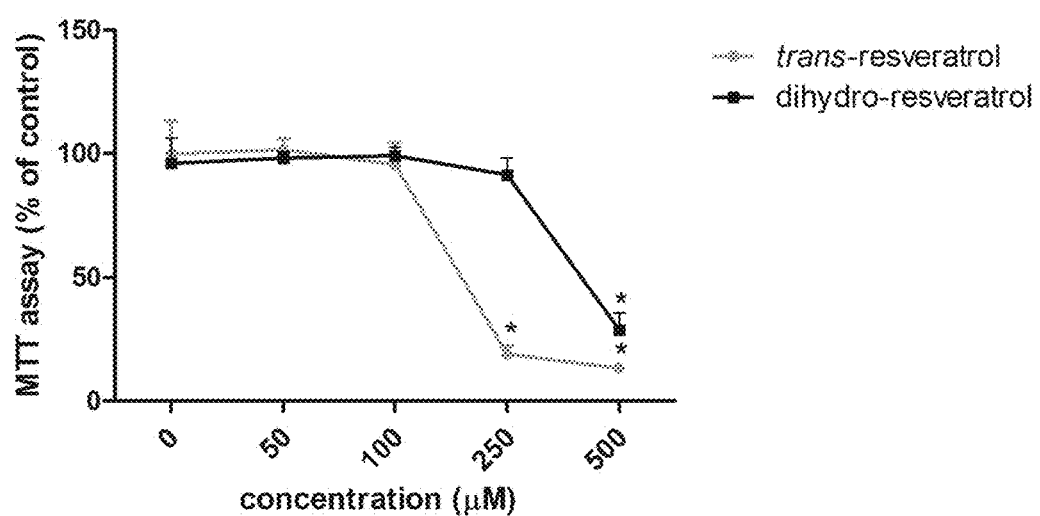

FIG. 7 shows the measurement of metabolic rates by means of MTT cell proliferation in pancreatic acinar cells treated with dihydro-resveratrol and trans-resveratrol. *p<0.05 when comparing with cells treated without dihydro-resveratrol or trans-resveratrol.

FIG. 8A to 8H shows eight derivatives (i.e. Compound i to Compound viii) from dihydro-resveratrol (i.e. Compound 2).

Figure 8A:
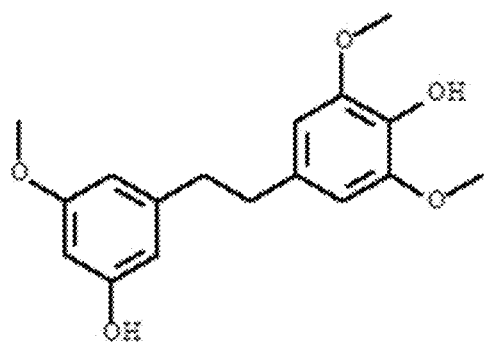
Figure 8B:
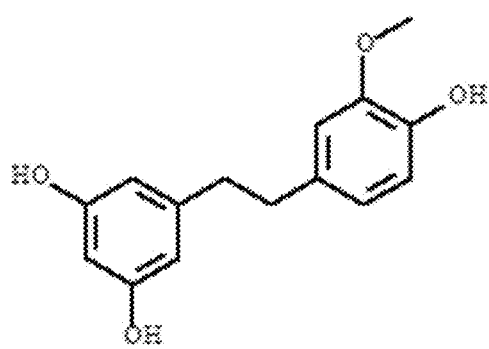
Figure 8C:
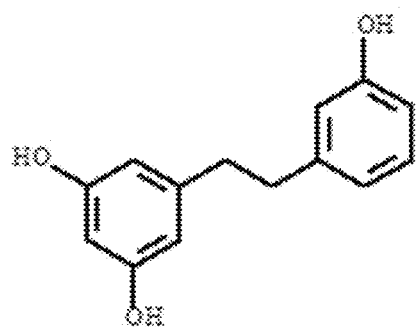
Figure 8D:
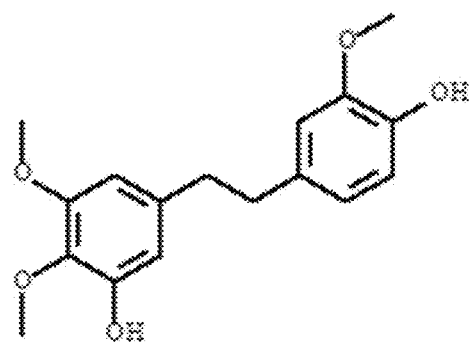
Figure 8E:
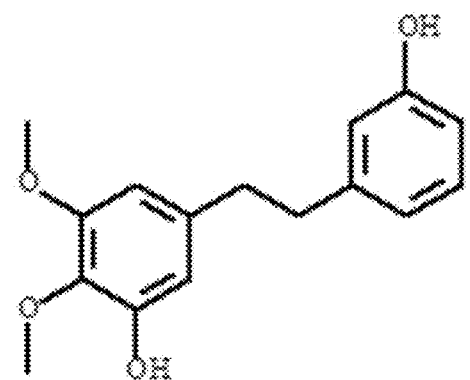
Figure 8F:
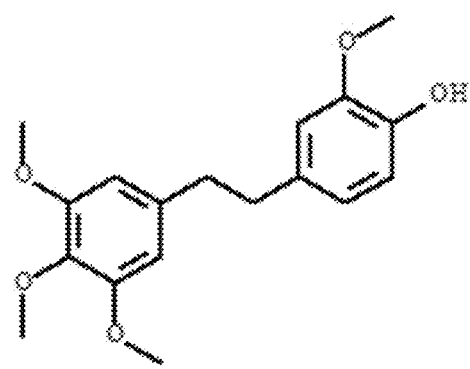
Figure 8G:
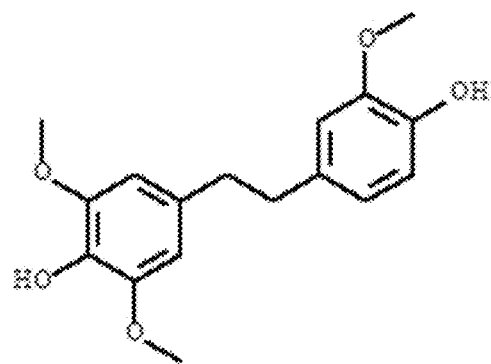
Figure 8H:
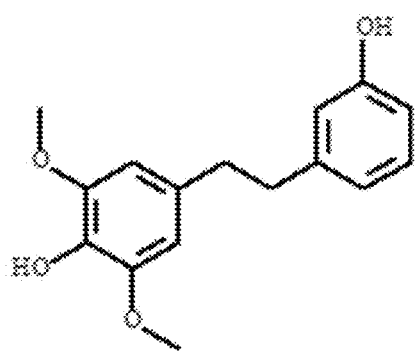
Figure 8I:
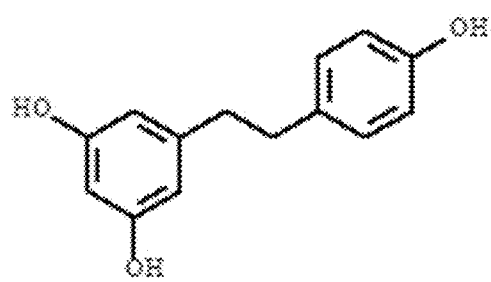

FIG. 8I shows the chemical structure of dihydro-resveratrol (i.e. Compound 2).

Figure 9:
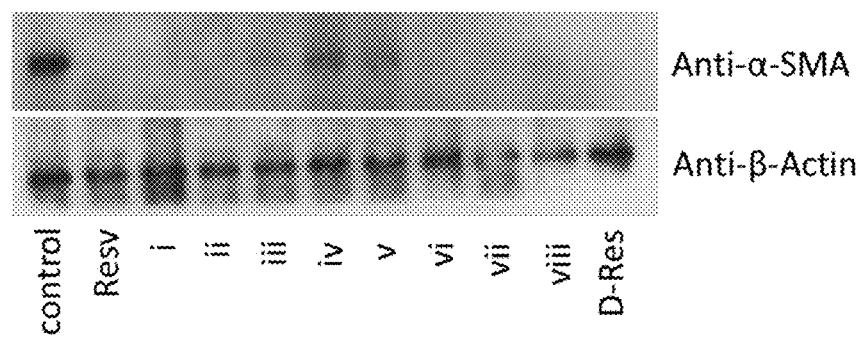

FIG. 9 shows Western blotting of LTC-14 PSCs pre-incubated with TGF-β (5 ng/mL), and treated with trans-resveratrol (Resv) or dihydro-resveratrol or stilbene compounds i to viii at 20 µg/mL for 24 hours. Control was not treated with Resv or any stilbenoids.

Figure 10:
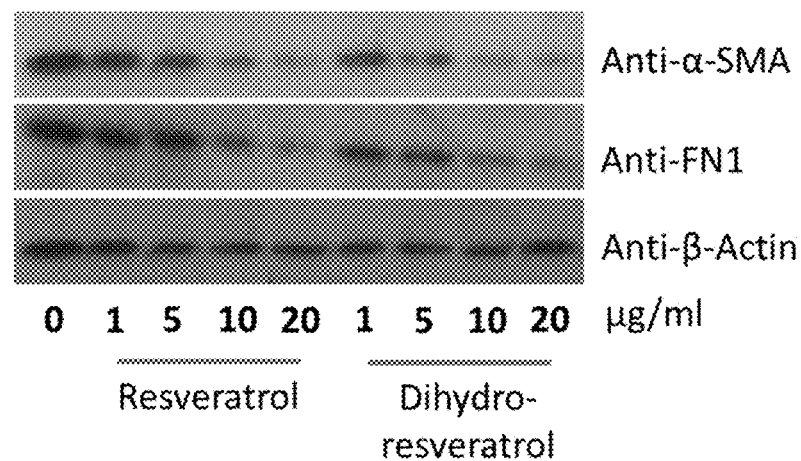

FIG. 10 shows the probing of α-SMA and FN1 in Western blotting of LTC-14 cells pre-incubated with TGF-β (5 ng/mL), and treated with trans-resveratrol or dihydro-resveratrol at the indicated concentrations.

Figure 11:
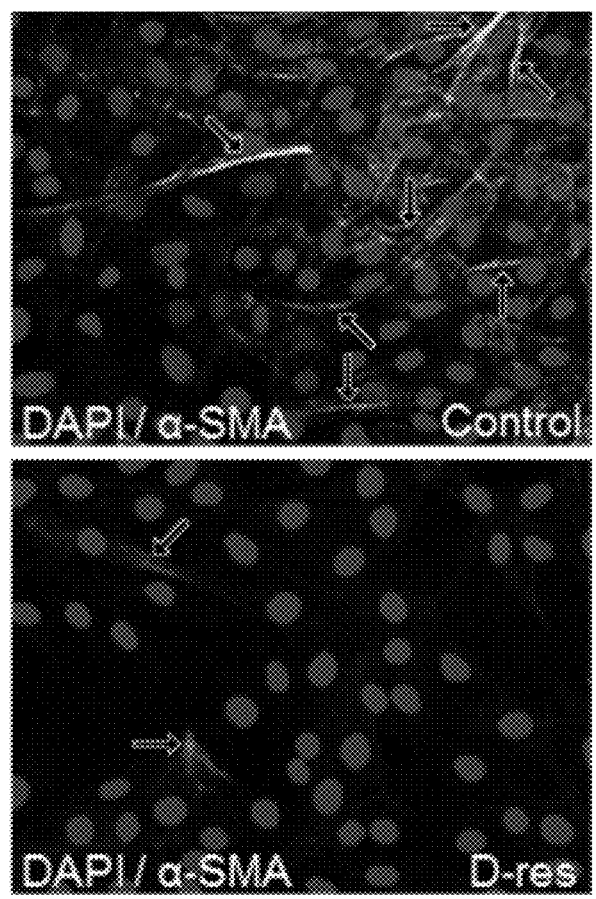

FIG. 11 shows the green fluorescent signal (identified by arrow marks) of fibrotic filaments α-SMA in LTC-14 cells implying the degree of PSC activation.

Figure 12:
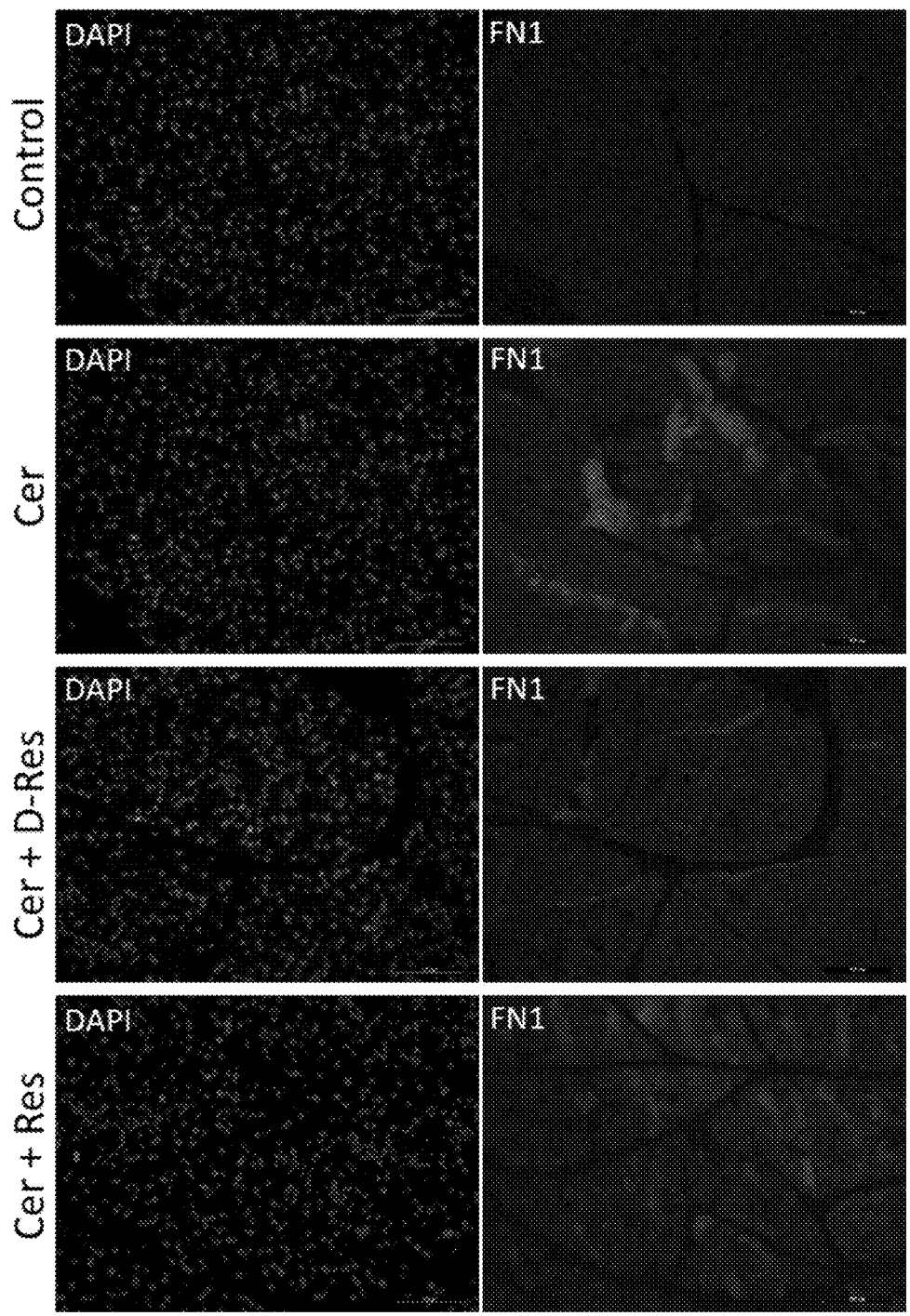

FIG. 12 shows the fluorescent signal of fibronectin (FN1) deposition in pancreatic tissue sections for an estimation of the degree of fibrosis with and without treatment of dihydro-resveratrol (D-Res, 20 mg/kg/day) or trans-resveratrol (Res, 20 mg/kg/day) in cerulein (Cer)-induced chronic pancreatitis mice.

Figure 13:
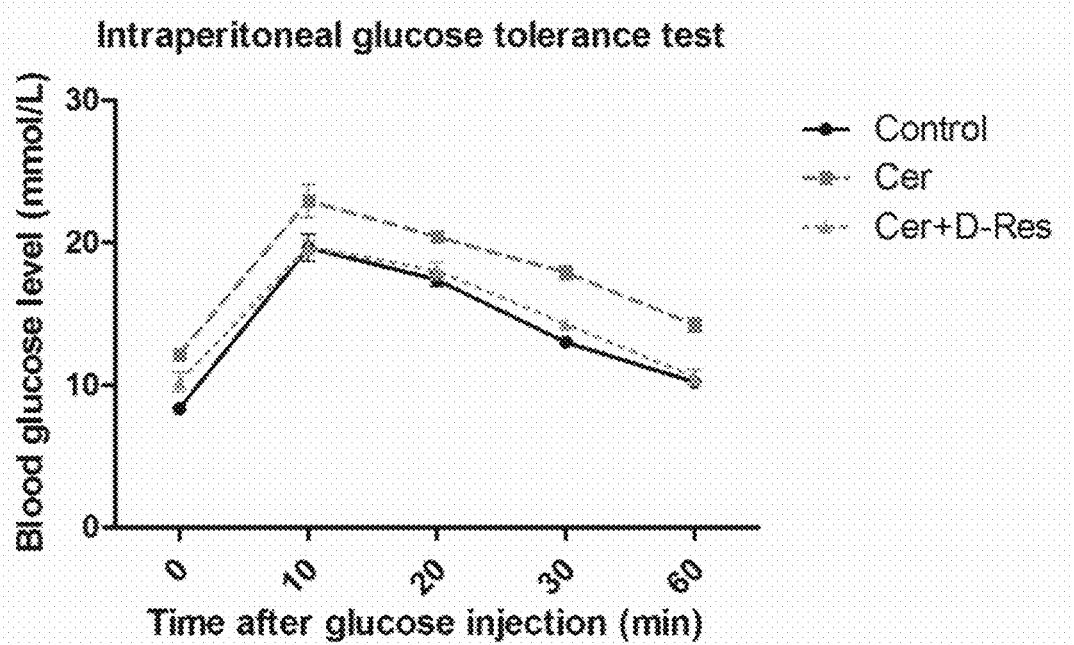

FIG. 13 shows the glucose response of the normal mice (Control) and chronic pancreatitis mice (Cer) with or without treatment of dihydro-resveratrol (D-Res, 20 mg/kg/day) in the intraperitoneal glucose tolerance test. At all time-points, a significant difference (p<0.05) is achieved between the Cer group and the Cer+D-Res group.

Figure 14:
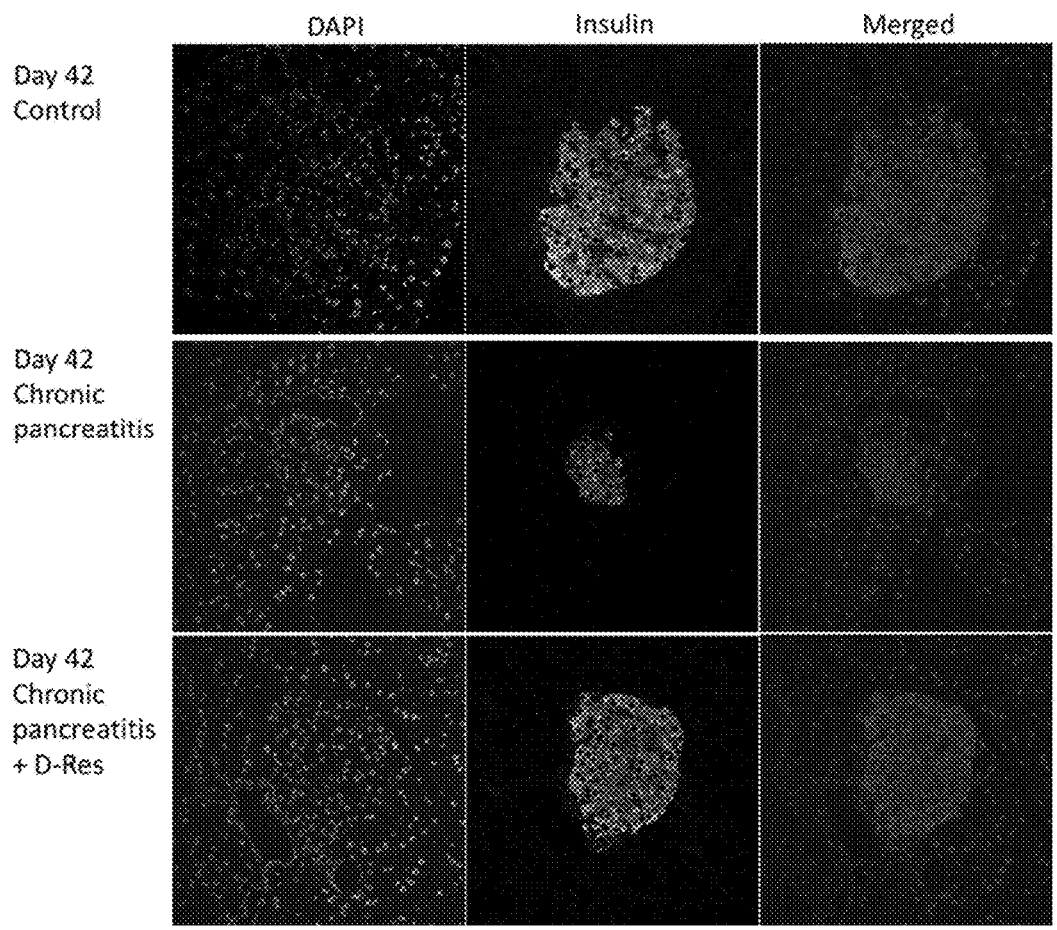

FIG. 14 shows the fluorescent signal of insulin in pancreatic tissue sections for an evaluation of pancreatic insulin-secreting cell (i.e. beta-cell) area. The comparison is made among the control mice, chronic pancreatitis mice and the chronic pancreatitis mice with treatment of dihydro-resveratrol (D-Res) at 20 mg/kg/day.

Figure 15:
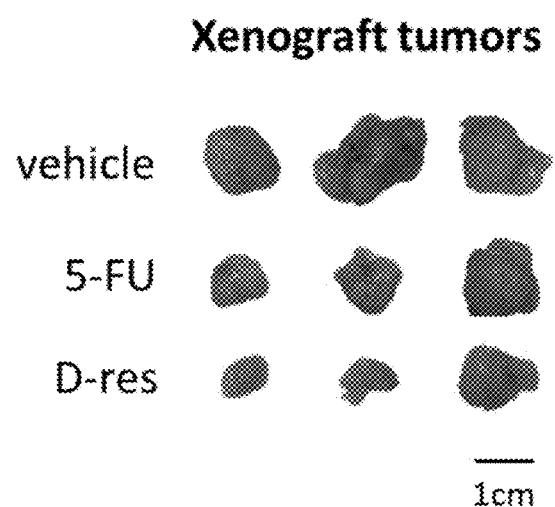

FIG. 15 shows the tumors obtained at the end of experiment from tumor-bearing mice treated with vehicle solution, 5-FU or D-res for 21 days.

Figure 16:
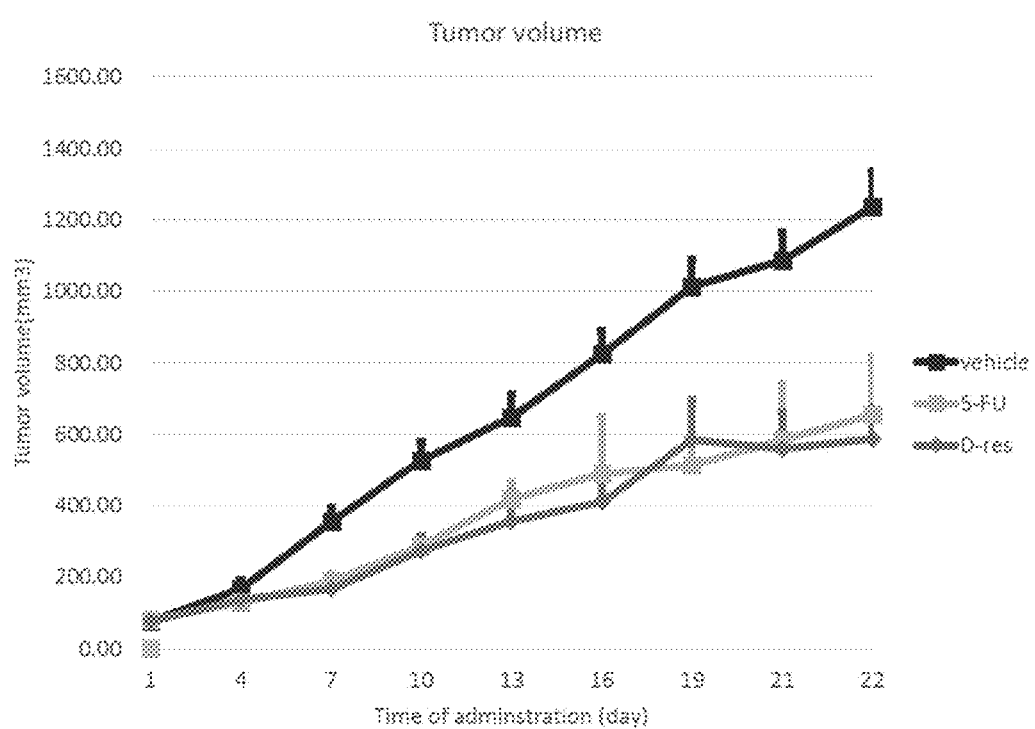

FIG. 16 shows the tumor size of tumor-bearing mice treated with vehicle solution, 5-FU or D-res. Tumor size was monitored by measuring the two perpendicular diameters with a caliper and expressed in terms of volume. Tumor volume (V) was calculated from equation: $V=0.5*(L \times W^2)$, where L is the length and W is the width in millimeters.

Figure 17:
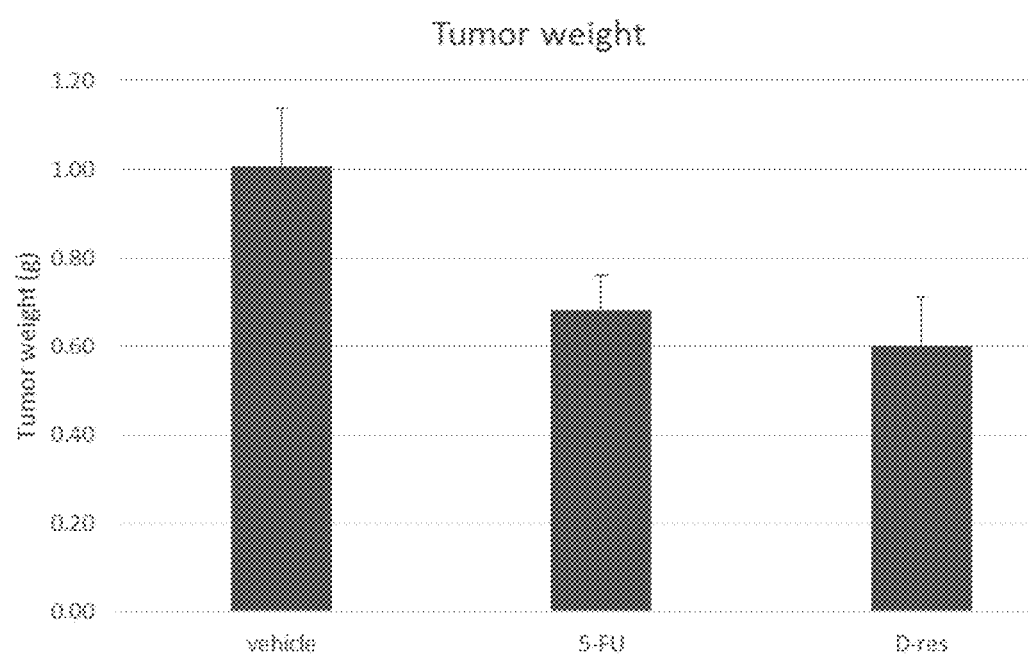

FIG. 17 shows the tumor weight of tumor-bearing nude mice treated with vehicle solution, 5-FU or D-res for 21 days.

Figure 18:
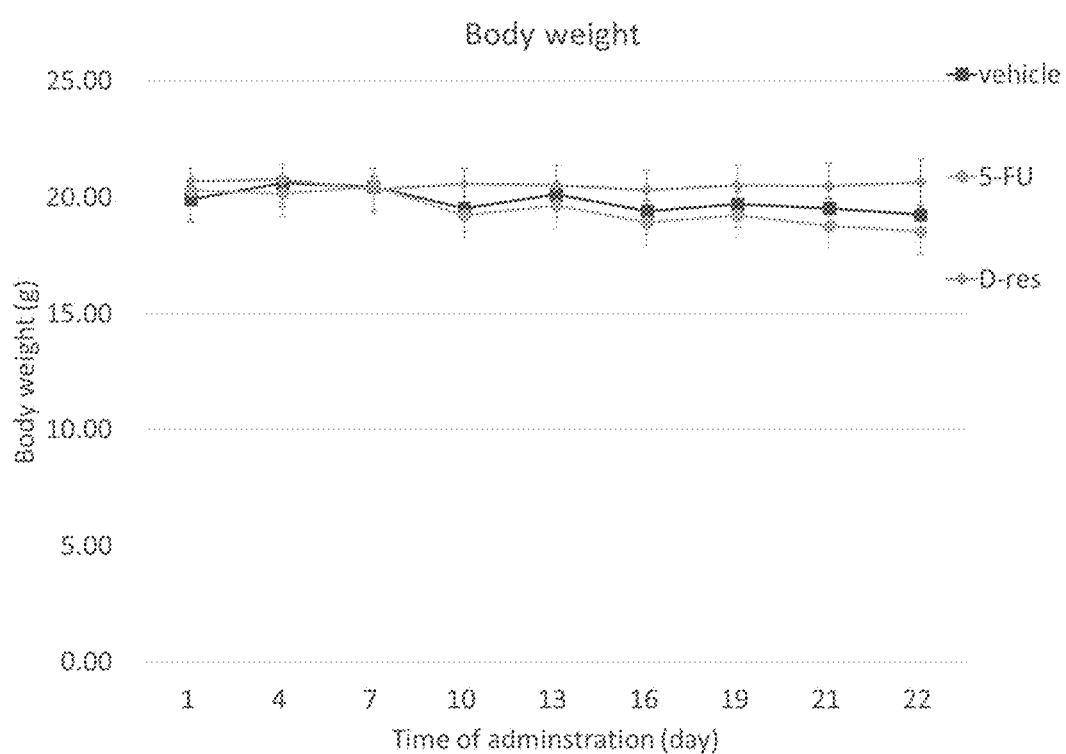

FIG. 18 shows the body weight of tumor-bearing nude mice treated with vehicle solution, 5-FU or D-res for 21 days.

FIG. 19 shows the suppressive effect of D-res on cell migration in human melanoma A375 cells (A) and human pancreatic ductal adenocarcinoma PANC-1 cells (B) post a 24-h treatment. DMSO serves as an experimental control.

Figure 20:
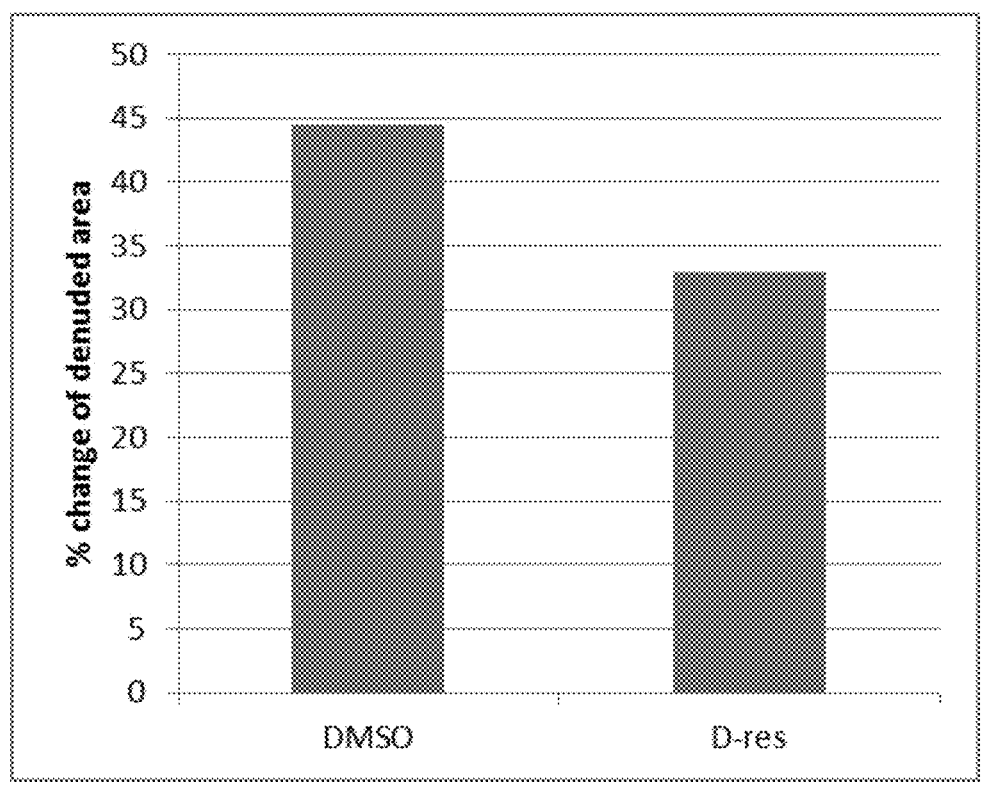

FIG. 20 shows the percentage change of the denuded area in PANC-1 cells upon the treatment of DMSO or D-res in the cell migration assay.

DETAILED DESCRIPTION OF INVENTION

The present invention is not to be limited in scope by any of the specific embodiments described herein. The following embodiments are presented for exemplification only.

Definitions

Hydrocarbyl

The term "hydrocarbyl" as used herein includes reference to a moiety consisting exclusively of hydrogen and carbon atoms; such a moiety may comprise an aliphatic and/or an aromatic moiety. The moiety may comprise 1, 2, 3, 4, 5, 6, 7, 8, 9, 10, 11, 12, 13, 14, 15, 16, 17, 18, 19 or 20 carbon atoms. Examples of hydrocarbyl groups include $C_{1-6}$ alkyl (e.g. $C_1$, $C_2$, $C_3$ or $C_4$ alkyl, for example methyl, ethyl, propyl, isopropyl, n-butyl, sec-butyl or tert-butyl); $C_{1-6}$ alkyl substituted by aryl (e.g. benzyl) or by cycloalkyl (e.g. cyclopropylmethyl); cycloalkyl (e.g. cyclopropyl, cyclobutyl, cyclopentyl or cyclohexyl); aryl (e.g. phenyl, naphthyl or fluorenyl) and the like.

Alkyl

The term "alkyl" as used herein includes reference to a straight or branched chain alkyl moiety having 1, 2, 3, 4, 5, 6, 7, 8, 9, 10, 11, 12, 13, 14, 15, 16, 17, 18, 19 or 20 carbon atoms. Examples of alkyl groups include "$C_{1-6}$ alkyl" and "$C_{2-10}$ alkyl". The term "$C_{1-6}$ alkyl" as used herein include reference to a straight or branched chain alkyl moiety having 1, 2, 3, 4, 5 or 6 carbon atoms. The term "$C_{2-10}$ alkyl" as used herein include reference to a straight or branched chain alkyl moiety having 1, 2, 3, 4, 5, 6, 7, 8, 9 or 10 carbon atoms. This term includes reference to groups such as methyl, ethyl, propyl (n-propyl or isopropyl), butyl (n-butyl, sec-butyl or tert-butyl), pentyl, hexyl and the like. In particular, the alkyl moiety may have 1, 2, 3, 4, 5 or 6 carbon atoms.

Alkenyl

The terms "alkenyl" and "$C_{2-6}$ alkenyl" as used herein include reference to a straight or branched chain alkyl moiety having 2, 3, 4, 5 or 6 carbon atoms and having, in addition, at least one double bond, of either E or Z stereochemistry where applicable. This term includes reference to groups such as ethenyl, 2-propenyl, 1-butenyl, 2-butenyl, 3-butenyl, 1-pentenyl, 2-pentenyl, 3-pentenyl, 1-hexenyl, 2-hexenyl and 3-hexenyl and the like.

Alkynyl

The terms "alkynyl" and "$C_{2-6}$ alkynyl" as used herein include reference to a straight or branched chain alkyl moiety having 2, 3, 4, 5 or 6 carbon atoms and having, in addition, at least one triple bond. This term includes reference to groups such as ethynyl, 1-propynyl, 2-propynyl, 1-butynyl, 2-butynyl, 3-butynyl, 1-pentynyl, 2-pentynyl, 3-pentynyl, 1-hexynyl, 2-hexynyl and 3-hexynyl and the like.

Alkoxy

The terms "alkoxy" and "$C_{1-6}$ alkoxy" as used herein include reference to —O-alkyl, wherein alkyl is straight or branched chain and comprises 1, 2, 3, 4, 5 or 6 carbon atoms. In one class of embodiments, alkoxy has 1, 2, 3 or 4 carbon atoms. This term includes reference to groups such as methoxy, ethoxy, propoxy, isopropoxy, butoxy, tert-butoxy, pentoxy, hexoxy and the like.

Cycloalkyl

The term "cycloalkyl" as used herein includes reference to an alicyclic moiety having 3, 4, 5, 6, 7 or 8 carbon atoms. The group may be a bridged or polycyclic ring system. More often cycloalkyl groups are monocyclic. This term includes reference to groups such as cyclopropyl, cyclobutyl, cyclopentyl, cyclohexyl, norbornyl, bicyclo[2.2.2]octyl and the like.

Aryl

The term "aryl" as used herein includes reference to an aromatic ring system comprising 6, 7, 8, 9, 10, 11, 12, 13, 14, 15 or 16 ring carbon atoms. Aryl is often phenyl but may be a polycyclic ring system, having two or more rings, at least one of which is aromatic. This term includes reference to groups such as phenyl, naphthyl, fluorenyl, azulenyl, indenyl, anthryl and the like.

Cyclic Group

"Cyclic group" means a ring or ring system, which may be unsaturated or partially unsaturated but is usually saturated, typically containing 5 to 13 ring-forming atoms, for example a 5- or 6-membered ring. The ring or ring system may be substituted with one or more hydrocarbyl groups. Cyclic group includes carbocyclyl and heterocyclyl moieties.

Carbocyclyl

The term "carbocyclyl" as used herein includes reference to a saturated (e.g. cycloalkyl) or unsaturated (e.g. aryl) ring moiety having 3, 4, 5, 6, 7, 8, 9, 10, 11, 12, 13, 14, 15 or 16 carbon ring atoms. In particular, carbocyclyl includes a 3- to 10-membered ring or ring system and, in particular, 5- or 6-membered rings, which may be saturated or unsaturated. The ring or ring system may be substituted with one or more hydrocarbyl groups. A carbocyclic moiety is, for example, selected from cyclopropyl, cyclobutyl, cyclopentyl, cyclohexyl, norbornyl, bicyclo[2.2.2]octyl, phenyl, naphthyl, fluorenyl, azulenyl, indenyl, anthryl and the like.

Heterocyclyl

The term "heterocyclyl" as used herein includes reference to a saturated (e.g. heterocycloalkyl) or unsaturated (e.g. heteroaryl) heterocyclic ring moiety having from 3, 4, 5, 6, 7, 8, 9, 10, 11, 12, 13, 14, 15 or 16 ring atoms, at least one of which is selected from nitrogen, oxygen, phosphorus, silicon and sulphur. In particular, heterocyclyl includes a 3- to 10-membered ring or ring system and more particularly a 5- or 6-membered ring, which may be saturated or unsaturated. The ring or ring system may be substituted with one or more hydrocarbyl groups.

A heterocyclic moiety is, for example, selected from oxiranyl, azirinyl, 1,2-oxathiolanyl, imidazolyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, pyrrolizidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, especially thiomorpholino, indolizinyl, isoindolyl, 3H-indolyl, indolyl, benzimidazolyl, cumaryl, indazolyl, triazolyl, tetrazolyl, purinyl, 4/V-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazoiyl, β-carbolinyl, phenanthridinyl, acridinyl, perimidinyl, phenanthrolinyl, furazanyl, phenazinyl, phenothiazinyl, phenoxazinyl, chromenyl, isochromanyl, chromanyl and the like.

Heterocycloalkyl

The term "heterocycloalkyl" as used herein includes reference to a saturated heterocyclic moiety having 3, 4, 5, 6 or 7 ring carbon atoms and 1, 2, 3, 4 or 5 ring heteroatoms selected from nitrogen, oxygen, phosphorus and sulphur. The group may be a polycyclic ring system but more often is monocyclic. This term includes reference to groups such as azetidinyl, pyrrolidinyl, tetrahydrofuranyl, piperidinyl, oxiranyl, pyrazolidinyl, imidazolyl, indolizidinyl, piperazinyl, thiazolidinyl, morpholinyl, thiomorpholinyl, quinolizidinyl and the like. The ring or ring system may be substituted with one or more hydrocarbyl groups.

Heteroaryl

The term "heteroaryl" as used herein includes reference to an aromatic heterocyclic ring system having 5, 6, 7, 8, 9, 10, 11, 12, 13, 14, 15 or 16 ring atoms, at least one of which is selected from nitrogen, oxygen and sulphur. The group may be a polycyclic ring system, having two or more rings, at least one of which is aromatic, but is more often monocyclic. The ring or ring system may be substituted with one or more hydrocarbyl groups. This term includes reference to groups such as pyrimidinyl, furanyl, benzo[b]thiophenyl, thiophenyl, pyrrolyl, imidazolyl, pyrrolidinyl, pyridinyl, benzo[b]furanyl, pyrazinyl, purinyl, indolyl, benzimidazolyl, quinolinyl, phenothiazinyl, triazinyl, phthalazinyl, 2H-chromenyl, oxazolyl, isoxazolyl, thiazolyl, isoindolyl, indazolyl, purinyl, isoquinolinyl, quinazolinyl, pteridinyl and the like.

Halogen

The term "halogen" as used herein includes reference to F, Cl, Br or I.

Halogen Containing Moiety

The expression "halogen containing moiety" as used herein includes reference to a moiety comprising 1 to 30 plural valence atoms selected from carbon, nitrogen, oxygen and sulphur which moiety includes at least one halogen. The moiety may be hydrocarbyl for example $C_{1-6}$ alkyl or $C_{1-6}$ alkoxy, or carbocyclyl for example aryl.

Substituted

The term "substituted" as used herein in reference to a moiety means that one or more, especially up to 5, more especially 1, 2 or 3, of the hydrogen atoms in said moiety are replaced independently of each other by the corresponding number of the described substituents. The term "optionally substituted" as used herein means substituted or un-substituted. It will, of course, be understood that substituents are only at positions where they are chemically possible, the person skilled in the art being able to decide (either experimentally or theoretically) without inappropriate effort whether a particular substitution is possible.

Enantiomer

The term "enantiomer" as used herein means one of two stereoisomers that have mirror images of one another.

Racemate

The term "racemate" as used herein means a mixture of equal amounts of enantiomers of a chiral molecule.

Diastereomer

The term "diastereomer" as used herein means one of a class of stereoisomers that are not enantiomers, but have different configurations at one or more of the equivalent chiral centers. Example of diastereomers are epimers that differ in configuration of only one chiral center.

Stereoisomer

The term "stereoisomer" as used herein means one of a class of isomeric molecules that have the same molecular formula and sequence of bonded atoms, but different three-dimensional orientations of their atoms in space.

Prodrug

A prodrug is a medication that is administered as an inactive (or less than fully active) chemical derivative that is subsequently converted to an active pharmacological agent in the body, often through normal metabolic processes.

Independently

Where two or more moieties are described as being "each independently" selected from a list of atoms or groups, this means that the moieties may be the same or different. The identity of each moiety is therefore independent of the identities of the one or more other moieties.

Embodiments of the present invention are described below. Preferred features of each aspect of the present invention are as for each of the other aspects mutatis mutandis. Moreover, it will be appreciated that the features specified in each embodiment may be combined with other specified features, to provide further embodiments.

Among the several established animal models, repetitive intraperitoneal (i.p.) injection of cholecystokinin secretagogue, cerulein, is the most widely used and a highly reproducible method for the production of an experimental acute pancreatitis. Followed by a single shot of lipopolysaccharide (LPS), pulmonary injury characterized by neutrophil sequestration in the lung tissues and increased permeability of the alveolar membrane barrier is often observed as an acute pancreatitis associated complication. For the diagnosis of the onset of acute pancreatitis, bulky leakage of digestive enzymes, namely α-amylase, into the bloodstream is regarded as the principal pathological parameter. For evaluating the severity of acute pancreatitis and the associated pulmonary injury, morphological alterations of organ architecture including interstitial edema, cellular damage, leukocyte infiltration and hemorrhage are characterized as the histological and/or pathological parameters. Besides histological examination, aberrant MPO activity is often measured for assessing the severity of neutrophil-mediated inflammatory condition. Both the local and systemic inflammatory responses can be further confirmed by the high levels of pro-inflammatory cytokines present in the homogenates of affected tissues. Moreover, glutathione depletion, a defense mechanism, is one of the most common parameters for assessing the severity of tissue injury.

The subject to be treated by the method of this invention may be a human or an animal. The present invention is applicable to various forms of acute pancreatitis, and particularly to the acute pancreatitis associated systemic complications including pulmonary injury.

Dihydro-resveratrol, also known as trans-3,5,4'-trihydroxybibenzyl, is a derivative of polyphenol belonging to the family of stilbenoids, which are often obtained from plant extracts. In fact, dihydro-resveratrol is a phytoalexin produced by various plant species including *Orchidaceae* and *Cannabis sativa* L. against abiotic and biotic challenges, particularly in the case of fungal infection as reported in Fritzemeier, K. H., Kindl, H. 1983. 9,10-dihydrophenanthrenes as phytoalexins of *Orchidaceae*. Biosynthetic studies in vitro and in vivo proving the route from L-phenylalanine to dihydro-m-coumaric acid, dihydrostilbene and dihydrophenanthrenes. Eur J Biochem 133, 545-550.

The present invention relates to the usage of a polyphenol derivative of the stilbenoid family with formula 1:

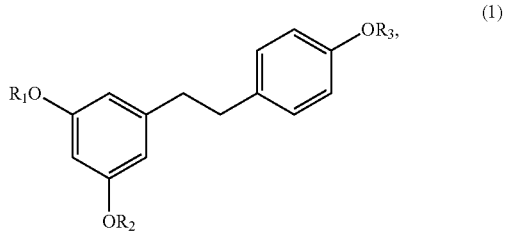

wherein $R_1$, $R_2$ and $R_3$ are each independently selected from an alkyl group. The term "alkyl", alone or in combination with other groups, includes reference to a straight chain alkyl moiety having 1, 2, 3, 4, 5 or 6 carbon atoms. The term is further exemplified by such groups as methyl, ethyl, propyl (n-propyl or isopropyl), butyl (n-butyl, sec-butyl and tert-butyl), pentyl, hexyl and the like, to ameliorate tissue injury of the pancreas and lungs.

The present invention further relates to the usage of a stilbene compound containing trans-3,5,4'-trihydroxybibenzyl, also known as dihydro-resveratrol, see Compound 2:

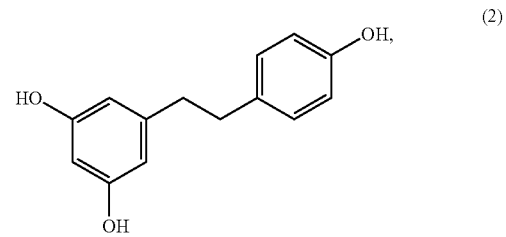 [SMILES: Oc1ccc(CCc2cc(O)cc(O)c2)cc1]

to ameliorate tissue injury of the pancreas and lungs. In the present invention, this particular stilbenoid derivative was obtained as white powders through hydrogenation of trans-resveratrol.

Further, the invention is concerned with a process for the manufacture of the above compound, pharmaceutical preparations which contain such compound, and the use of this compound for the production of pharmaceutical preparations.

Figure 1:
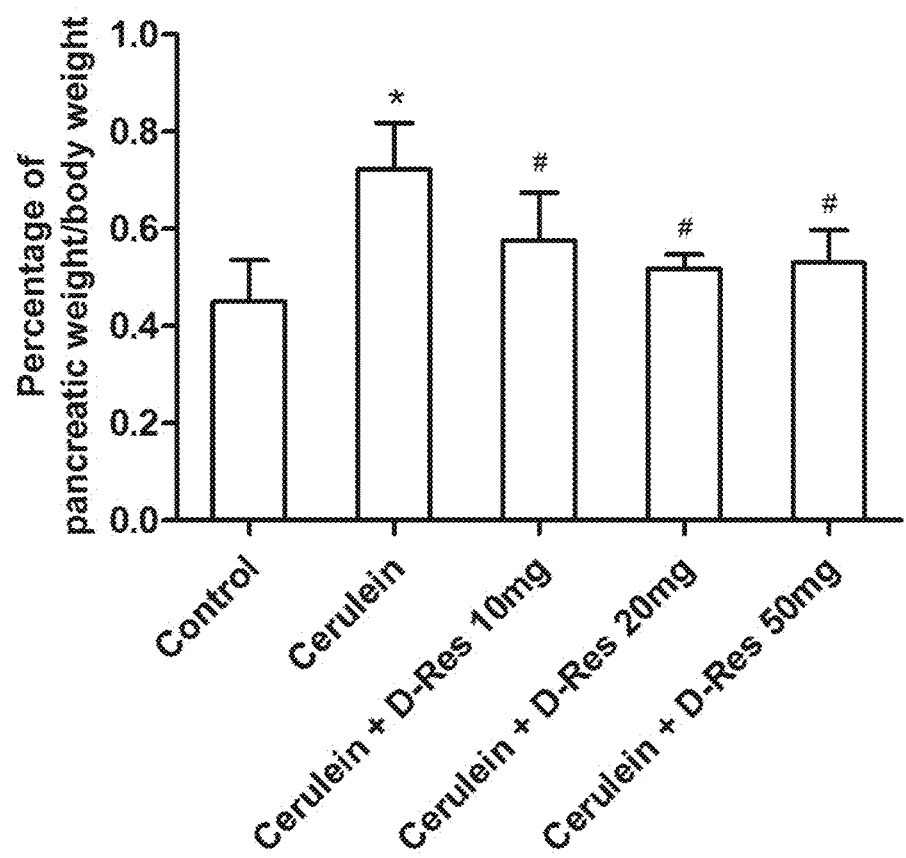
FIG. 1 shows the gain of water content in rats due to effect of pancreatic edema as a result of cerulein-induced acute pancreatitis. The obtained weights are expressed as a ratio percentage of pancreatic weight to body mass. A p-value of less than 0.05 is considered as statistically significant. *$p<0.05$ when comparing with control group whereas #$p<0.05$ comparing with cerulein group.

The oral administration of dihydro-resveratrol at an adequate dosage of not less than 20 mg/kg is shown to significantly ameliorate the severity of acute pancreatitis and associated pulmonary injury in cerulein-treated rats. In terms of pathological parameters, rats with acute pancreatitis are shown to have lessened pancreatic water content due to an attenuation of pancreatic edema (FIG. 1), lowered plasma level of α-amylase (Table 1), more intact acinar morphology (FIGS. 2C to 2F) and reduced thickening of alveolar wall and hemorrhage (FIGS. 3C to 3E).

TABLE 1

Plasma α-amylase activities are expressed as U/μl/minute.
A p-value of less than 0.05 is considered as statistically
significant and S.D. stands for standard derivation.

|  | Control | Cerulein | Cerulein + D-Res 10 mg | Cerulein + D-Res 20 mg | Cerulein + D-Res 50 mg |
|---|---|---|---|---|---|
| mean | 0.1294 | 0.4846 * | 0.2891 | 0.2498 # | 0.2431 # |
| S.D. | 0.03909 | 0.1457 | 0.05248 | 0.05593 | 0.06025 |

\* p < 0.05 when comparing with control group whereas
\# p < 0.05 comparing with cerulein group.

Figure 4A:
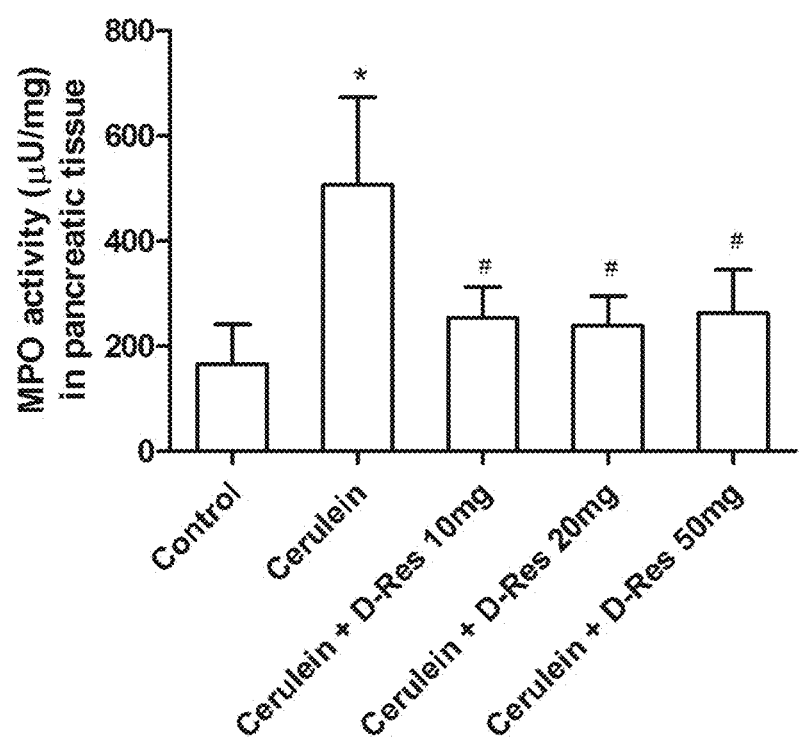
FIG. 4A shows the measurement of MPO activity which represents neutrophil sequestration in pancreatic tissues of control group, cerulein group and dihydro-resveratrol treatment groups (D-Res) by means of colorimetric spectrophotometry. A p-value of less than 0.05 is considered as statistically significant. *$p<0.05$ when comparing with control group whereas #$p<0.05$ comparing with cerulein group.
Figure 4B:
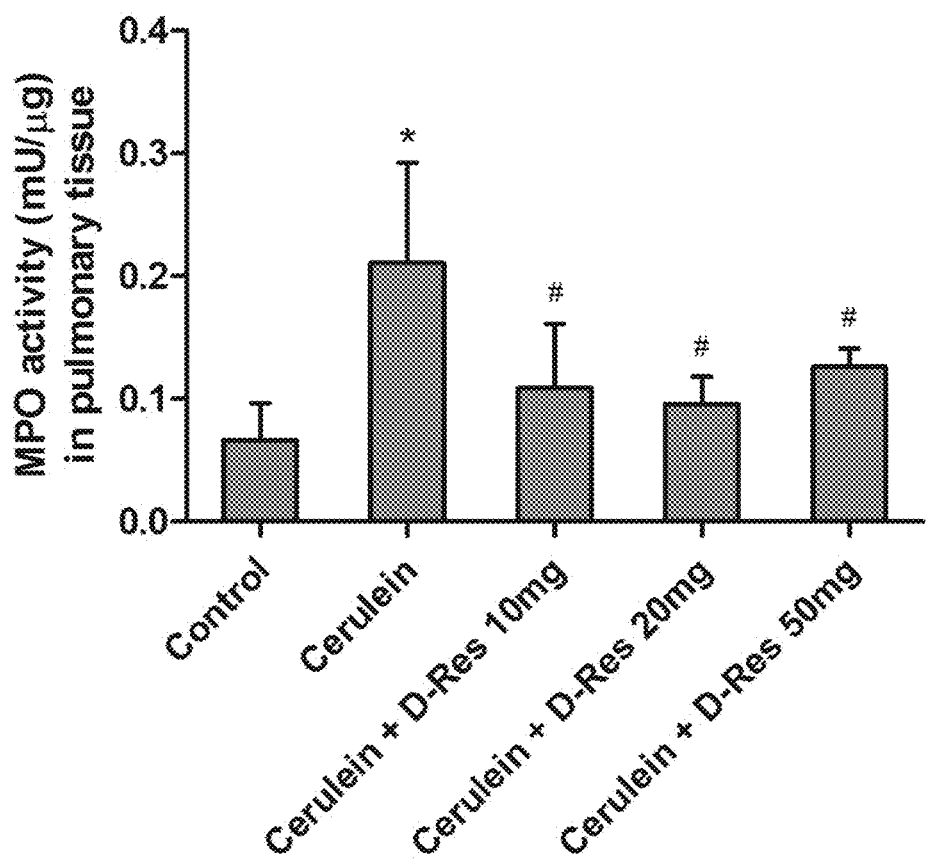
FIG. 4B shows the measurement of MPO activity which represents neutrophil sequestration in pulmonary tissues of control group, cerulein group and dihydro-resveratrol treatment groups (D-Res) by means of colorimetric spectrophotometry. A p-value of less than 0.05 is considered as statistically significant. *$p<0.05$ when comparing with control group whereas #$p<0.05$ comparing with cerulein group.
Figure 5A:
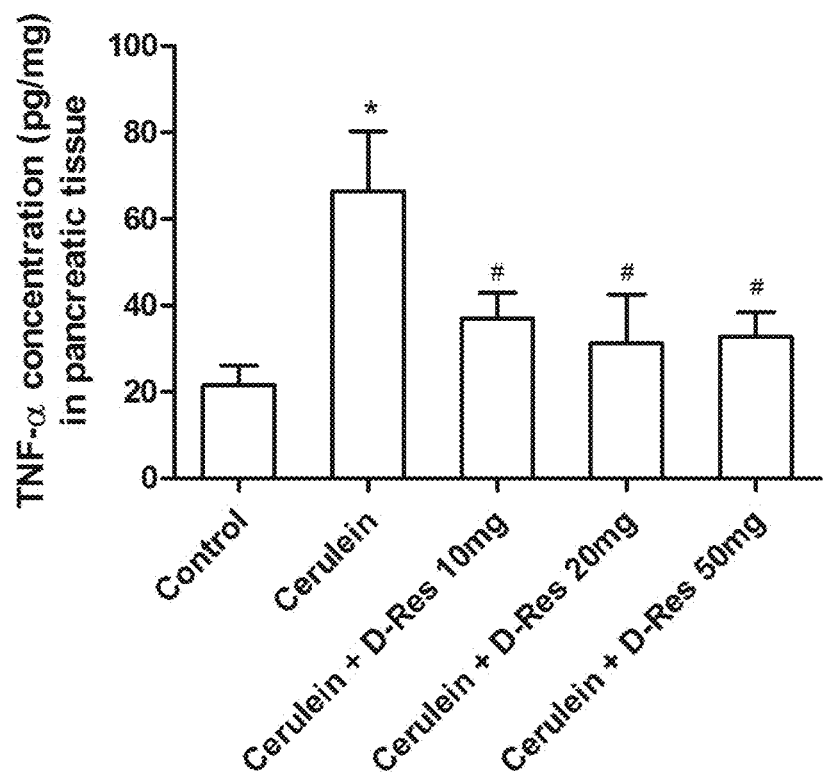
FIG. 5A shows the measurement of TNF-α level in pancreatic tissues of control group, cerulein group and dihydro-resveratrol treatment groups (D-Res) by means of enzyme-linked immunosorbent assay (ELISA). A p-value of less than 0.05 is considered as statistically significant. *$p<0.05$ when comparing with control group whereas #$p<0.05$ comparing with cerulein group.
Figure 5B:
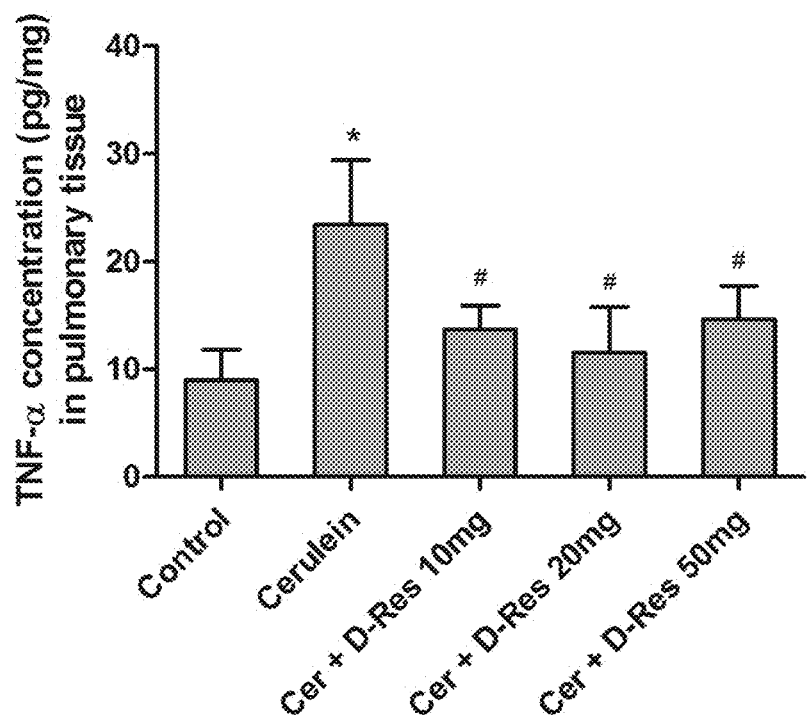
FIG. 5B shows the measurement of TNF-α level in pulmonary tissues of control group, cerulein group and dihydro-resveratrol treatment groups (D-Res) by means of ELISA. A p-value of less than 0.05 is considered as statistically significant. *$p<0.05$ when comparing with control group whereas #$p<0.05$ comparing with cerulein group.

Cerulein-induced elevated levels of neutrophil sequestration, which is quantified as the activity of MPO, are significantly suppressed in pancreatic and pulmonary tissues by the administration of dihydro-resveratrol (FIGS. 4A and 4B). Cerulein-induced elevated levels of TNF-α in the pancreas and lungs are significantly suppressed by the administration of dihydro-resveratrol (FIGS. 5A and 5B).

Glutathione depletion is a distinctive sign of tissue injury. The cerulein-induced declined levels of glutathione in the pancreas are significantly restored by the administration of dihydro-resveratrol (FIG. 6A).

In the present invention, dihydro-resveratrol completely and easily dissolves in 0.5% (weight/volume, w/v) methanol whereas trans-resveratrol, with vigorous shaking, dissolves in 2.5% (w/v) methanol (Table 2). Thus, the solubility of dihydro-resveratrol is at least 5 times higher than that of trans-resveratrol. The ameliorative effect of dihydro-resveratrol was more promising than that of trans-resveratrol on reducing water content as a result of pancreatic edema in rats with cerulein-induced acute pancreatitis (FIG. 6B).

TABLE 2

Solubility of Dihydro-resveratrol and Trans-resveratrol in methanol.

|  | Trans-resveratrol | Dihydro-resveratrol |
| --- | --- | --- |
| Methanol required (w/v) | 2.5% | 0.5% |

From the evaluation of mitochondrial metabolic rates by means of MTT assay, the cytotoxicity of dihydro-resveratrol in pancreatic acinar cells is determined to be approximately 500 μM whereas that of trans-resveratrol is roughly 250 μM (FIG. 7). Thus, the cytotoxicity of dihydro-resveratrol was 50% lower than that of trans-resveratrol.

Experiments

Preparation and structural identification of dihydro-resveratrol. The molecular formula of dihydro-resveratrol was established as $C_{14}H_{14}O_3$, which was obtained as white powders through hydrogenation of trans-resveratrol. A solution of trans-resveratrol (10 g, 43.8 mmol) in anhydrous EtOH (150 ml) was stirred at room temperature under 5 atm $H_2$ pressure in the presence of 10% Pd/C (0.2 g). The reaction was quenched after 8 hours (h), by filtering off the catalyst. The filtrate was evaporated in vacuum and the residue was subjected to silica gel chromatographic separation eluting with petroleum ether and ethyl acetate (1:1) to afford dihydro-resveratrol as white amorphous powder (9.6 g, 95% yield): HR-ESIMS ([M+1]+ m/z 231.1026, calcd 231.1016 for $C_{14}H_{15}O_3$); $^1$H NMR (methanol-d4, 400 MHz) δ 6.96 (2H, ABd, J=8.3 Hz), 6.67 (2H, ABd, J=8.4 Hz), 6.13 (2H, brd, J=2.2 Hz), 6.09 (1H, brt, J=2.2 Hz), 2.74 (2H, brdd, J=8.5, 5.6), 2.67 (2H, brdd, J=8.3, 5.2); $^{13}$C NMR (methanol-d4, 100 MHz) δ 159.2 (2C, s), 156.3 (1C, s), 145.6 (1C, s), 134.1 (1C, s), 130.3 (2C, d), 116.0 (2C, d), 108.1 (2C, d), 101.1 (1C, d), 39.6 (2C, t), 38.0 (2C, t).

Evaluation of biological activities. Sprague-Dawley rats aged 28 days weighing in the range of 70 to 90 g were randomly assigned into 6 groups of 6 to 8 individuals. The rats were housed with an ambient temperature of 23±2° C., a relative humidity of 60 to 80% and a 12-h light/dark cycle. Prior to the experiment, the rats were starved overnight but allowed with free access to water. Experimental acute pancreatitis was induced in the rats by six hourly i.p. injections of cerulein at the supramaximally stimulating dose (50 μg/kg) followed by a single dose of LPS at 7.5 mg/kg 1 h after the last cerulein injection, and this group of rats was designated as the cerulein group. The control group received injections of 0.9% saline instead of cerulein in the same volume and at same time intervals. The treatment groups given with cerulein and oral doses of dihydro-resveratrol (10, 20 or 50 mg/kg) were designated as Cerulein+D-res 10 or 20 or 50 mg/kg. The therapeutic intervention was given 30 minutes after the first cerulein injection for three consecutive hours. Upon scarification, pancreata were immediately removed, weighed, trimmed from fat and fixed in 4% paraformaldehyde-phosphate buffered saline overnight at 4° C. Samples were then processed, embedded in paraffin wax, sectioned and subjected to H&E staining. Levels of TNF-α in pancreatic and pulmonary samples were determined using commercial ELISA kits. Tissue homogenates were subjected to biochemical assays for the evaluation of MPO activity and glutathione content.

Functional intact acini were dissociated from pancreatic tissue using collagenase digestion with mild shearing forces. Acini were cultured in Dulbecco's modification of Eagle's medium (GIBCO) supplemented with 5% fetal bovine serum (GIBCO), 1% penicillin-streptomycin (GIBCO) in a 5% $CO_2$, 95% air humidified atmosphere at 37° C. LTC-14 cells were seeded at a density of $1\times10^4$/well in a 96-well plate, and incubated with different concentrations of dihydro-resveratrol or trans-resveratrol (dissolved in DMSO) for 24 hours. MTT reagent was added to the cells at the end of the 24-hour treatment period. After a 3-hour reaction time, MTT products were dissolved in DMSO and absorbance at 570 nm was taken.

Results

After the induction of cerulein, the weight ratio of pancreas to body in the acute pancreatitis rats drastically increased by roughly 60% when compared with the non-cerulein induced controls due to the occurrence of pancreatic edema. The oral administration of dihydro-resveratrol at an adequate dosage of not less than 20 mg/kg notably reduced the pancreatic edema as reflected by the significant decrease in the weight ratio of pancreas to body. The ameliorative effect of dihydro-resveratrol on reducing pancreatic edema was more promising than that of trans-resveratrol, the accredited antioxidant. Regarding the human dosage, the comparable dosage is 3.24 mg/kg based on the standard dosage conversion according to Reagan-Shaw S, Nihal M, Ahmad N (2008) Dose translation from animal to human studies revisited. FASEB J 22(3): 659-661.

When oral administration of dihydro-resveratrol was given, the focal expansion of the interlobular septae, cytoplasmic shrinkage and leukocyte infiltration in pancreatitic parenchyma was remarkably reduced whereas the pulmonary wall thickening and hemorrhage in lung tissues were significantly improved in the rats with cerulein-induced acute pancreatitis.

For a relief of inflammatory conditions of the pancreas and lungs, the levels of pro-inflammatory cytokine TNF-α as well as MPO activities were significantly reduced in the pancreatic and pulmonary tissues by the oral administration of dihydro-resveratrol.

The level of glutathione in cerulein-induced pancreatic tissue was depleted drastically by more than 50% when compared to the non-cerulein-treated control. The oral administration of dihydro-resveratrol significantly suppressed glutathione depletion in the cerulein-induced pancreata.

The solubility of dihydro-resveratrol in a methanol-based solvent was at least 5 times higher than that of trans-resveratrol. By assessing the mitochondrial metabolic rates of acini, the cytotoxicity of dihydro-resveratrol was shown to be approximately 500 μM whereas that of trans-resveratrol was roughly 250 μM. Thus, the cytotoxicity of dihydro-resveratrol was 50% lower than that of trans-resveratrol.

In a first embodiment of a first aspect of the present invention there is provided a method of treating acute inflammatory condition of the pancreas and associated systemic complications by administering to a subject in needs thereof a composition comprising an effective amount of a stilbenoid derivative which comprises a compound of formula (1),

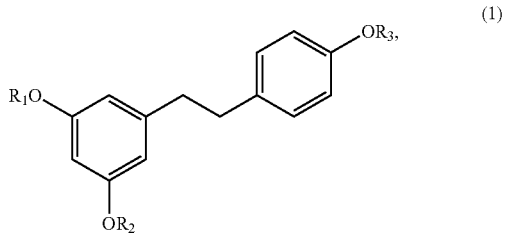

wherein $R_1$, $R_2$ and $R_3$ are each independently selected from an alkyl group. The term "alkyl", alone or in combination with other groups, includes reference to a straight chain alkyl moiety having 1, 2, 3, 4, 5 or 6 carbon atoms. The term is further exemplified by such groups as methyl, ethyl, propyl (n-propyl or isopropyl), butyl (n-butyl, sec-butyl and tert-butyl), pentyl, hexyl and the like, and the derivatives or chemical variants thereof; or a mixture of said compound, the derivative and/or chemical variants thereof.

In a second embodiment of a first aspect of the present invention there is provided a method of treating acute inflammatory condition of the pancreas and associated systemic complications wherein the stilbenoid derivative is trans-3,5,4'-trihydroxybibenzyl, or dihydro-resveratrol, which is a compound of formula (2):

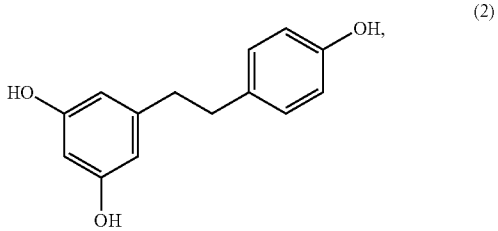 [SMILES: Oc1ccc(CCc2cc(O)cc(O)c2)cc1]

and the derivatives or chemical variants thereof; or a mixture of said compound, the derivative and/or chemical variants thereof.

In a third embodiment of the first aspect of the present invention there is provided a method of treating acute inflammatory condition of the pancreas and associated systemic complications wherein the subject is a human or an animal.

In a fourth embodiment of the first aspect of the present invention there is provided a method of treating acute inflammatory condition of the pancreas and associated systemic complications wherein the composition is administered orally.

In a fifth embodiment of the first aspect of the present invention there is provided a method of treating acute inflammatory condition of the pancreas and associated systemic complications wherein the acute inflammatory condition of the pancreas comprises all forms of acute pancreatitis and associated systemic complications comprise pulmonary injury.

In a sixth embodiment of the first aspect of the present invention there is provided a method of treating acute inflammatory condition of the pancreas and associated systemic complications wherein said composition is administered at no less than 20 mg/kg to said subject for no less than 3 times a day.

In a seventh embodiment of the first aspect of the present invention there is provided a method of treating acute inflammatory condition of the pancreas and associated systemic complications wherein said composition is administered at no less than 3.24 mg/kg to said subject for no less than 3 times a day.

In a first embodiment of a second aspect of the present invention there is provided a method for preparing a compound of molecular formula $C_{14}H_{14}O_3$ and of formula (2),

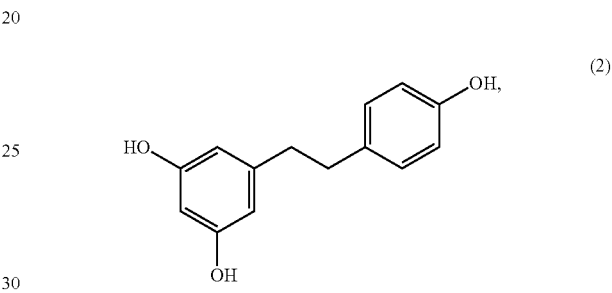

which is a stilbenoid derivative having a chemical name of trans-3,5,4'-trihydroxybibenzyl by hydrogenating of trans-resveratrol.

In a second embodiment of the second aspect of the present invention there is provided a method of preparing the compound of molecular formula $C_{14}H_{14}O_3$ and of formula (2) wherein the hydrogenating of trans-resveratrol comprises steps of
  stirring a solution of trans-resveratrol in anhydrous EtOH at room temperature under 5 atm $H_2$ pressure in the presence of 10% Pd/C for 8 hours;
  filtering off the catalyst from the stirred solution;
  evaporating the filtrate in vacuum to produce a residue;
  eluting the residue using silica gel chromatographic separation with petroleum ether and ethyl acetate (1:1) to produce dihydro-resveratrol.

Further Embodiments of the Present Invention

TGF-β has been reported by some previous studies as a potent inducer of PSC activation in which a series of fibrotic mediators, including FN1, are being up-regulated. In cultured LTC-14 cells, which are immortalized PSCs from rat, the expression levels of fibrotic filament α-SMA and ECM protein FN1 are remarkably elevated by the exogenous addition of recombinant TGF-β (5 ng/mL). In one further embodiment of the present invention, the inventors discover that the administration of dihydro-resveratrol significantly attenuate the expression levels of α-SMA and FN1 in rat PSCs upon the challenge of TGF-β. The derivatives of dihydro-resveratrol exert similar suppressive effect in PSCs. When compared to the renowned anti-oxidant trans-resveratrol, the inhibitory effect of dihydro-resveratrol is more significant. Among the testing stilbenoids, dihydro-resveratrol exerts the most potent anti-fibrotic effect in PSCs despite they possess modest structural differences.

The present invention provides a compound for suppressing a fibrotic mediator of stellate cells present in an internal organ of a subject in need with a formula of

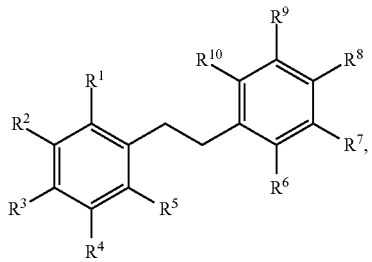

(3)

wherein $R^2$ and $R^4$ are each independently selected from —$OR^{11}$ and —$OC(O)R^{11}$;

$R^1$, $R^3$, $R^5$, $R^6$, $R^7$, $R^8$, $R^9$ and $R^{10}$ are each independently selected from hydrogen, halogen, trifluoromethyl, —$OR^{11}$ and —$OC(O)R^{11}$; or $R^2$ and $R^3$, or $R^7$ and $R^8$ may be taken together with the carbon atoms to which they are attached to form a cyclic group;

$R^{11}$ is independently hydrogen or selected from hydrocarbyl and heterocyclyl, either of which is optionally substituted with 1, 2, 3, 4 or 5 $R^{12}$;

$R^{12}$ is independently selected from halogen, trifluoromethyl, cyano, nitro, oxo, —$OR^{13}$, —$C(O)R^{14}$, —$C(O)N(R^{13})R^{14}$, —$C(O)OR^{13}$, —$OC(O)R^{14}$, —$S(O)_2R^{13}$, —$S(O)_2N(R^{13})R^{14}$, —$N(R^{13})R^{14}$;

$R^{13}$ and $R^{14}$ are each independently hydrogen or selected from hydrocarbyl and heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy;

or an enantiomer thereof;

or a pharmaceutically acceptable salt or prodrug thereof;

or a mixture of said compound, the derivative and/or chemical variants thereof.

The present invention further provides nine embodiments of compounds for suppressing a fibrotic mediator of stellate cells present in an internal organ of a subject in need with formula of:

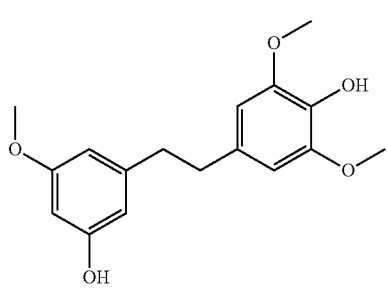

(i)

4-[2-(3-Hydroxy-5-methoxyphenyl)ethyl]-2,6-dimethoxy-phenol

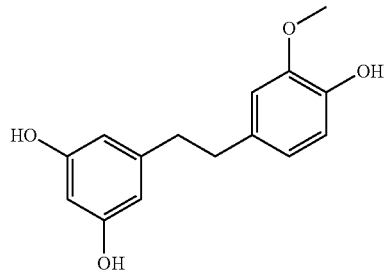

(ii)

Tristin

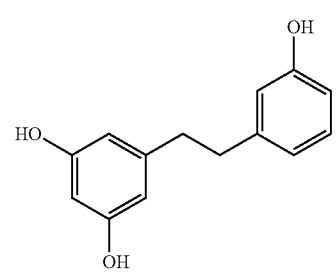

(iii)

3,3',5-Trihydroxydibenzyl

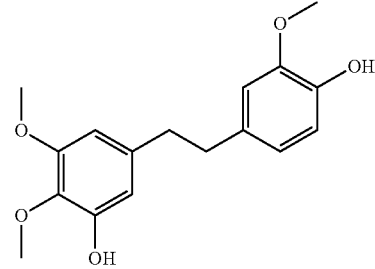

(iv)

5-[2-(4-Hydroxy-3-methoxyphenyl)ethyl]-2,3-dimethoxy-phenol

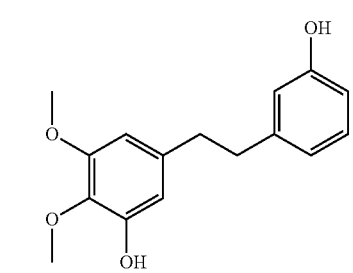

(v)

5-[2-(3-Hydroxyphenyl)ethyl]-2,3-dimethoxy-phenol (vi)

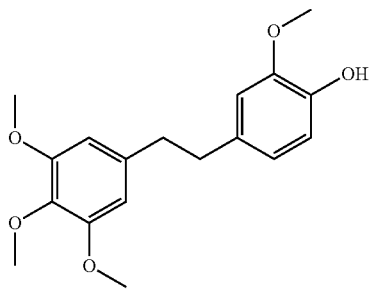

Crepidatin (vii)

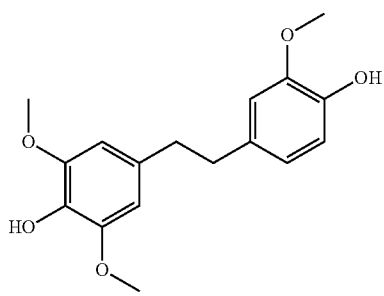

Moscatilin (viii)

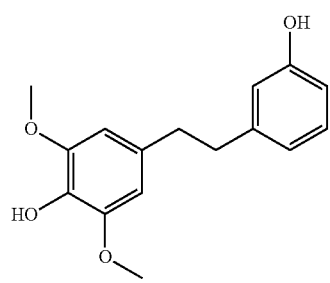

Aloifol I (2)

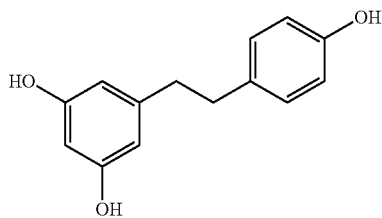

dihydro-resveratrol

The internal organ can be, for example, pancreas, liver, kidney and lung of a subject. The subject can be a human subject.

Experiments:

LTC-14 cells were cultured at 37° C. under a humidified condition of 95% air and 5% $CO_2$ in IMDM supplemented with 10% fetal bovine serum (FBS). Cells used in all the experiment were among passages 9 to 25. LTC-14 cells were seeded at a density of $1 \times 10^5$/well in a 12-well plate, and incubated with recombinant TGF-β at 5 ng/mL with dihydro-resveratrol at 0, 1, 5, 10 and 20 μg/mL in IMDM supplemented with 0.2% FBS for 24 hours. Cells were then harvested for protein extraction and Western blotting analysis or immunofluorescent staining.

Total proteins of the LTC-14 cells are extracted using RIPA lysis buffers containing protease inhibitors. Cell lysates were loaded and separated by SDS-polyacrylaminde gel electrophoresis. After wet electroblotting, proteins were transferred onto PVDF membranes (Bio-rad), blocked with 5% non-fat milk, probed with antibodies and visualized by utilization of an ECL kit (GE Healthcare).

For immunofluorescent staining of α-SMA, LTC-14 cells were seeded at a density of $1 \times 10^5$ onto the poly-L-lysine-coated cover slips in a 24-well plate, incubated with TGF-β at 5 ng/mL with dihydro-resveratrol at 0, and 10 μg/mL in IMDM supplemented with 0.2% FBS for 24 hours. Cells were then fixed, blocked with 3% BSA, probed with antibodies and mounted with fluorescence mounting medium containing 4',6-diamidino-2-phenylindole (DAPI). Images were captured using the Nikon microscope and analyzed by the SPOT advanced software.

Evaluation of biological activities. C57/BL6 mice aged 28 days weighing in the range of 20 to 25 g were randomly assigned into 4 groups of 6 to 8 individuals. The mice were housed with an ambient temperature of 23±2° C., a relative humidity of 60 to 80% and a 12-h light/dark cycle. Prior to the glucose tolerance test, the mice were starved overnight but allowed with free access to water. Experimental chronic pancreatitis was induced in the mice by four hourly intraperitoneal injections of cerulein at the supramaximally stimulating dose (50 μg/kg/h) a day, 3 days a week, in a total of 6 weeks. The control group received injections of 0.9% saline instead of cerulein in the same volume and at same time intervals. The treatment groups given with cerulein and oral doses of dihydro-resveratrol (20 mg/kg/day) were designated as Cer+D-res. A dosage of dihydro-resveratrol at 50 mg/kg/day had also been attempted in the treatment course, but no statistically significant difference from the dose at 20 mg/kg/day in fibrosis formation was achieved. Nevertheless, no adverse effect was obtained from this higher dosage in the in vivo trial. Thus, it concludes that an effective dosage of dihydro-resveratrol is at least 20 mg/kg/day. The group given with trans-resveratrol was designated as Cer+Res. The drug intervention of both compounds was given from the first day of week 4 till the end of experiment, i.e. in a total of 3 weeks. At the end of the 6-week experiment, mice were subjected to the intraperitoneal glucose tolerance test (IP-GTT). Mice had been starved for 14 hours prior to the IPGTT, in which a 15% (w/v) glucose solution was injected to individual animals at 1.5 g glucose per kg body weight. About 1 μL of blood will be obtained from the tail vein, and blood glucose levels were monitored using a glucometer (Medisign, Korea) 30 min before (i.e. fasting level) and 10, 20, 30 and 60 min after glucose injection. Upon scarification, pancreases were immediately removed, weighed, trimmed from fat and fixed in 4% paraformaldehyde-phosphate buffered saline overnight at 4° C. Samples were then processed, embedded in paraffin wax, sectioned and subjected to immunostaining.

According to the dose translation formula, human equivalent dosage (mg/kg)=Animal dose (mg/kg) multiplied by animal Km/human Km, where mouse Km is 3 and human Km is 37 (Guidance for Industry Estimating the Maximum Safe Starting Dose in Initial Clinical Trials for Therapeutics in Adult Healthy Volunteers), the effective human equivalent dosage of dihydro-resveratrol of the present invention is at least 1.622 mg/kg/day.

In yet another embodiment of the present invention, 8 other derivatives (compounds i to viii) of dihydro-resveratrol and (compound 2) dihydro-resveratrol are shown in FIGS. 8A-8I. In this embodiment, each compound is experimented accordingly as follows:

Experiment with the Embodiments of Compounds in FIGS. 8A-8I

LTC-14 cells were pre-incubated with TGF-β (5 ng/mL), and treated with trans-resveratrol (Resv) or dihydro-resveratrol (D-Res) or stilbene compounds i-viii at 20 μg/mL for 24 hours. Control was not treated with Resv or any stilbenoids. Total proteins were extracted and analyzed using Western blotting. This is shown in FIG. 9.

LTC-14 cells are pancreatic stellate cells. α-SMA is the hallmark component of fibrogenesis whereas β-actin serves as a loading control. Thus, the expression level of α-SMA implies the degree of PSC activation. TGF-β was added since it is regarded as a potent inducer of fibrotic events. Suppressive effect on α-SMA expression level is tested among dihydro-resveratrol and compounds i to viii in relation to trans-resveratrol (Resv). All of the testing compounds exert suppressive effect of α-SMA expression level.

LTC-14 cells were pre-incubated with TGF-β (5 ng/mL), and treated with trans-resveratrol or dihydro-resveratrol at the indicated concentrations. Total proteins were extracted and analyzed using Western blotting. This is shown in FIG. 10.

FN1 is a major extracellular matrix protein produced during fibrogenesis or upon the activation of pancreatic stellate cells. Its expression level implies the degree of fibrogenesis. Suppressive effect on levels of FN1 and α-SMA is tested between dihydro-resveratrol (i.e. compound 2) and trans-resveratrol.

LTC-14 cells were pre-incubated with TGF-β (5 ng/mL), and treated with dihydro-resveratrol at 20 μg/mL for 24 hours prior to immunofluorescent staining.

LTC-14 cells are pancreatic stellate cells. α-SMA is the hallmark component of fibrogenesis whereas β-actin serves as a loading control. Thus, the green fluorescent signal (identified by arrow marks in FIG. 11) of α-SMA implies the degree of PSC activation. TGF-β was added since it is regarded as a potent inducer of fibrotic events. Suppressive effect of dihydro-resveratrol on α-SMA expression level is tested.

Pancreatic tissue sections are stained with antibody against FN1; thus, the immunostaining signals imply the degree of FN1 deposition in the parenchyma. The treatment with dihydro-resveratrol at 20 mg/kg/day (Cer+D-Res) reduces such deposition in chronic pancreatitis in a manner more significant to trans-resveratrol (Cer+Res). This is shown in FIG. 12.

Evaluation of biological activities. C57/BL6 mice aged 28 days weighing in the range of 20 to 25 g were randomly assigned into 4 groups of 6 to 8 individuals. The mice were housed with an ambient temperature of 23±2° C., a relative humidity of 60 to 80% and a 12-h light/dark cycle. When oral administration of dihydro-resveratrol (20 mg/kg/day) is given, the fasting blood glucose levels of the chronic pancreatitis mice (Cer) become markedly higher than those of the control group, indicating these chronic pancreatitis mice develop hyperglycemia, a discernible feature of diabetes. Importantly, their impaired glucose tolerance has been significantly rectified by the 3-week dihydro-resveratrol treatment (Cer+D-Res). As a result, the hyperglycemic condition of the chronic pancreatitis mice is improved. This is shown in FIG. 13.

When oral administration of dihydro-resveratrol (Cer+D-Res) is given at 20 mg/kg/day, the severity of pancreatitis and the shrinkage and destruction of islets, explicitly beta cells, are notably ameliorated. As shown in FIG. 14, the pancreatic beta-cell area is reflected by the immunofluorescent insulin signals. A reduced beta-cell area or mass implicates the deficiency in glucose tolerance, or the development of diabetes. Thus, the restoration of beta-cell area by the dihydro-resveratrol treatment indicates this stilbenoid is beneficial to the treatment of pancreatogenic diabetes (i.e. Type3c DM).

According to the dose translation formula, human equivalent dosage (mg/kg)=Animal dose (mg/kg) multiplied by animal Km/human Km, where mouse Km is 3 and human Km is 37 (Guidance for Industry Estimating the Maximum Safe Starting Dose in Initial Clinical Trials for Therapeutics in Adult Healthy Volunteers), the effective human equivalent dosage of dihydro-resveratrol of the present invention is at least 1.622 mg/kg/day.

Another Embodiment of the Present Invention

Dihydro-resveratrol described herein restrains the growth of xenograft tumor, in terms of weight and volume, without exhibiting undesirable side-effect in the experimental animals. Though possessing eminent structural similarity to trans-resveratrol, dihydro-resveratrol undergoes no further metabolic breakdown in the human bowel and exists as a colonic metabolite upon microbial conversion. Thus, dihydro-resveratrol can act as an alternative remedy to trans-resveratrol for patients with microbial restriction and receive unresponsiveness.

Experimental Animals

All animal studies were approved and performed according to Animal Care and Use Guidelines of the Animal Ethics Committee at Hong Kong Baptist University. BALB/c nude mice, SPF class, male, 6-8 weeks old, were purchased from BioLASCO, Taiwan. Before the xenograft experiment, the mice were acclimatized to SPF class laboratory conditions for a week.

Cell Culture and Cell Viability Assay

The human colorectal carcinoma HCT-116 cell line, human pancreatic ductal adenocarcinoma PANC-1 cell line, human melanoma A375 cell line and human embryonic kidney HEK293 cell line were purchased from the American Type Culture Collection. Cells were cultured in high glucose DMEM growth medium supplemented with 10% fetal bovine serum, penicillin and streptomycin (100 U) in a humidified atmosphere of 5% $CO_2$, 95% air at 37° C. Upon the addition of dihydro-resveratrol (D-res) to the HCT-116, PANC-1, A375 or HEK293 cells seeded at a density of 8000 cells per well in a 96-well plate format, the viability of the testing cells was determined 24 h post treatment using the (3-(4,5-dimethylthiazol-2-yl)-2,5-diphenyltetrazolium bromide) tetrazolium (MMT) reduction assay and expressed as growth inhibition of 50% ($GI_{50}$, Table 3).

TABLE 3

The GI$_{50}$ of dihydro-resveratrol in various kinds of carcinoma cells

| Cell line | Type of cells with human origin | GI$_{50}$ |
|---|---|---|
| A375 | Melanoma | 106.59 ± 3.37 μM |
| HCT-116 | Colorectal carcinoma | 102.04 ± 5.21 μM |
| HEK293 | Embryonic kidney (serves as normal control) | 244.11 ± 0.96 μM |
| PANC-1 | Pancreatic ductal adenocarcinoma | 115.69 ± 3.09 μM |

Establishment of the Nude Mouse Xenograft Model

HCT-116 cells in logarithmic growth phase were collected by trypsinization. After centrifugation and rinsing, cells were re-suspended in serum-free DMEM medium at $3\times10^7$ cells/mL. Nude mice were skin disinfected with 75% medical ethanol, subcutaneously injected with 100 μL of the HCT-116 cell suspension using a 25-G syringe to their left flank. The same procedure was repeated for the tumor cell injection to the right flank.

Animal Grouping

Seven days after tumor cell injection, 24 mice with tumor volumes of 32 mm$^3$ to 178 mm$^3$ were randomly assigned into 3 groups; the average initial tumor volumes in each group of mice were 78.04±7.76 mm$^3$ (vehicle, 8 mice), 78.76±9.40 mm$^3$ (5-FU, 8 mice), 78.01±7.75 mm$^3$ (D-res, 8 mice) respectively.

Preparation of Drug Regimen and Vehicle

Vehicle solution: 2.5% Ethanol and Cremphor EL (1:1 v/v) dissolved in physiological saline.

5-FU solution: 5-FU powder was dissolved in 2.5% Ethanol and Cremphor EL to a concentration of 5 mg/mL.

D-res solution: Dihydro-resveratrol powder was dissolved in 2.5% Ethanol and Cremphor EL solution to a concentration of 20 mg/mL.

Dosage Regimen

Vehicle group (n=8): 2.5% Ethanol and Cremphor EL solution was intraperitoneally injected every other day for 21 days.

5-FU group (n=8): 5-FU solution was given to mice at 25 mg/kg by intraperitoneal injection every other day for 21 days.

D-res group (n=8): D-res solution was given to mice at 100 mg/kg by intraperitoneal injection every other day for 21 days. This is equivalent to a dosage of no less than 8.13 mg/kg of bodily weight in human.

The growth of xenograft tumor derived from HCT-116 human colorectal carcinoma cells, in terms of tumor size (FIG. 15), tumor volume (FIG. 16) and tumor weight (FIG. 17), is more sufficiently restrained by the 21-day administration of D-res when comparing to the mainstay anticancer drug 5-FU. The numerical data and statistics of tumor volume, tumor weight and body weight of the tumor-bearing mice are respectively provided in Tables 4, 5 and 6. It is worth noting that the 21-day administration of D-res does not lead to a significant loss of body weight (FIG. 18). Such result implies that D-res is not a toxic substance that causes severe undesirable effects in animals. Apart from the in vivo experiments, the application of D-res (25 μM) indeed exhibits significant reduction in the migratory ability of A375 human melanoma cells and PANC-1 human pancreatic ductal adenocarcinoma cells in vitro (FIG. 19). The percentage change of denuded area, which denotes cellular migratory ability, in PANC-1 cells after the 24-h treatment of D-res or DMSO (i.e. the experimental control) is presented in FIG. 20. Further, the GI$_{50}$ values in Table 3 imply that D-res has a selectivity towards carcinoma cells.

The effective dosage of D-res ranges from 20 mg/kg (body weight) to 100 mg/kg (body weight) per day. According to the dose translation formula (Nair A B, Jacob S. A simple practice guide for dose conversion between animals and human. J Basic Clin Pharma 2016; 7:27-31.) Eq. (2), the effective translated human dose of D-res of the present invention ranges from 1.62 mg/kg (body weight) to 8.13 mg/kg (body weight) per day.

TABLE 4

Tumor volume (mm$^3$) of HCT-116 human colorectal carcinoma-bearing nude mice treated with vehicle solution, fluorouracil (5-FU) and dihydro-resveratrol (D-res) for 21 days

| Group | Tumor volume (mm$^3$) Day | | | | | | | | |
|---|---|---|---|---|---|---|---|---|---|
| | 1 | 4 | 7 | 10 | 13 | 16 | 19 | 21 | 22 |
| vehicle | 78.04 ± 7.76 | 168.51 ± 24.08 | 355.2 ± 39.65 | 526.61 ± 53.45 | 648.07 ± 65.55 | 826.04 ± 65.55 | 1013.95 ± 76.21 | 1087.09 ± 79.85 | 1236.94 ± 100.21 |
| 5-FU | 78.76 ± 9.40 | 128.05 ± 12.25 | 187.75 ± 21.56 | 286.6 ± 28.89 | 419.1 ± 45.77 | 489.8 ± 160.66 | 514.17 ± 160.66 | 583.6 ± 160.66 | 655.69 ± 160.66 |
| D-Res | 78.01 ± 7.75 | 137.54 ± 14.69 | 167.58 ± 22.65 | 273.28 ± 41.5 | 355.48 ± 78.57 | 409.35 ± 74.3 | 585.98 ± 110.96 | 559.76 ± 100.63 | 586.92 ± 88.51 |

The differences in tumor volume between the D-res group and vehicle group whereas between the 5-FU group and vehicle group were statistically significant $P < 0.001$.

TABLE 5

Tumor weight (g) of HCT-116 human colorectal carcinoma-bearing nude mice treated with vehicle solution, fluorouracil (5-FU) and dihydro-resveratrol (D-res) for 21 days

| Groups | Tumor weight (g) |
|---|---|
| vehicle | 1.01 ± 0.13 |
| 5-FU | 0.68 ± 0.08 |
| D-res | 0.60 ± 0.11 |

The differences in tumor weight between the D-res group and vehicle group whereas between the 5-FU group and vehicle group were statistically significant $P < 0.05$.

TABLE 6

Body weight (g) of HCT-116 human colorectal carcinoma-bearing nude mice treated with vehicle solution, fluorouracil (5-FU) and dihydro-resveratrol (D-res) for 21 days.

| Group | Body weight (g) Day | | | | | | | | |
|---|---|---|---|---|---|---|---|---|---|
| | 1 | 4 | 7 | 10 | 13 | 16 | 19 | 21 | 22 |
| vehicle | 19.91 ± 0.37 | 20.6 ± 0.32 | 20.45 ± 0.42 | 19.54 ± 0.5 | 20.14 ± 0.49 | 19.41 ± 0.44 | 19.71 ± 0.51 | 19.53 ± 0.43 | 19.27 ± 0.39 |
| 5-FU | 20.3 ± 0.46 | 20.16 ± 0.55 | 20.46 ± 0.48 | 19.24 ± 0.46 | 19.65 ± 0.46 | 18.94 ± 0.47 | 19.23 ± 0.52 | 18.79 ± 0.59 | 18.54 ± 0.59 |
| D-res | 20.69 ± 0.55 | 20.76 ± 0.65 | 20.33 ± 0.9 | 20.57 ± 0.66 | 20.53 ± 0.82 | 20.31 ± 0.88 | 20.51 ± 0.87 | 20.5 ± 0.94 | 20.63 ± 0.99 |

The administration of D-res did not lead to a notable reduction in body weight of the experimental nude mice.

INDUSTRIAL APPLICABILITY

The present invention relates to a polyphenol derivative of the stilbenoid family, namely trans-3,5,4'-trihydroxybibenzyl, also known as dihydro-resveratrol, as a remedial agent. In particular, the present invention presents the usage of dihydro-resveratrol or its derivatives/chemical variants in the manufacture of a medicament for the treatment of tumors or cancers. The dihydrostilbenes can be used in the treatment or delay of progression of a cancer in a patient or used in a pharmaceutical formulation for the aforementioned purposes.

What we claim:

1. A method of treating colorectal, melanoma and pancreatic carcinoma by administering to a subject in need thereof an effective dosage of a compound of formula (2)

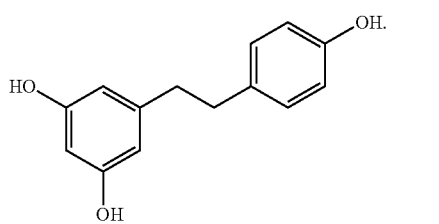

(2)

2. The method according to claim 1 wherein said compound is dihydro-resveratrol.

3. The method according to claim 1 wherein said compound is trans-3,5,4'-trihydroxybibenzyl.

4. The method according to claim 1 wherein said effective dosage ranges from 1.62 mg/kg to 8.13 mg/kg in body weight per day.

5. The method according to claim 1 wherein said effective dosage is 8.13 mg/kg in body weight per day.

6. The method according to claim 4 wherein said subject is human.

7. The method according to claim 5 wherein said subject is human.

8. The method according to claim 1 wherein said compound is administered in situ to site of the colorectal, melanoma and pancreatic carcinoma.

9. The method according to claim 8 wherein said compound is administered intraperitoneally to said subject in need thereof.

10. The method according to claim 1 wherein said subject is human.

11. The method according to claim 1 wherein the compound is administered every other day for an effective period of time.

12. The method according to claim 11 wherein said effective period of time is no less than 21 days.

* * * * *